US012622953B2

(12) United States Patent
Kringelum et al.

(10) Patent No.: US 12,622,953 B2
(45) Date of Patent: May 12, 2026

(54) VACCINES TARGETING NEOEPITOPES

(71) Applicants:Evaxion Biotech A/S, Hørsholm (DK); Staten Serum Institut, Copenhagen S. (DK)

(72) Inventors: Jens Kringelum, Hørsholm (DK); Anders Bundgård Sørensen, Hrosholm (DK); Birgitte Rønø, Hørsholm (DK); Nadia Viborg Petersen, Hørsholm (DK); Signe Tandrum Schmidt, Copenhagen (DK); Lars Vibe Andreasen, Copenhagen (DK); Dennis Christensen, Copenhagen (DK)

(73) Assignees: Evaxion A/S, Hørsholm (DK); Statens Serum Institut, Copenhagen S. (DK)

( * ) Notice: Subject to any disclaimer, the term of this patent is extended or adjusted under 35 U.S.C. 154(b) by 1100 days.

(21) Appl. No.: 17/420,315

(22) PCT Filed: Jan. 3, 2020

(86) PCT No.: PCT/EP2020/050058
§ 371 (c)(1),
(2) Date: Jul. 1, 2021

(87) PCT Pub. No.: WO2020/141207
PCT Pub. Date: Jul. 9, 2020

(65) Prior Publication Data
US 2022/0062397 A1 Mar. 3, 2022

(30) Foreign Application Priority Data
Jan. 3, 2019 (EP) ..................................... 19150200
Nov. 5, 2019 (EP) ..................................... 19207238

(51) Int. Cl.
*A61K 39/00* (2006.01)
*A61P 35/00* (2006.01)

(52) U.S. Cl.
CPC .......... *A61K 39/0011* (2013.01); *A61K 39/00* (2013.01); *A61P 35/00* (2018.01); *A61K 2039/545* (2013.01); *A61K 2039/55555* (2013.01)

(58) Field of Classification Search
CPC .... A61K 39/0011; A61K 39/00; A61K 39/39; A61K 35/00; A61K 2039/545; A61K 2039/55555
See application file for complete search history.

(56) References Cited

U.S. PATENT DOCUMENTS

2014/0112979 A1 4/2014 Andreasen et al.
2016/0228528 A1 8/2016 Jungersen et al.
2017/0224799 A1* 8/2017 Srivastava ......... G01N 33/6878
2018/0094032 A1 4/2018 Bedu-Addo et al.

FOREIGN PATENT DOCUMENTS

| | | |
|---|---|---|
| CN | 103619325 | 3/2014 |
| WO | WO2013004234 | 1/2013 |
| WO | WO2017106638 | 6/2017 |
| WO | WO2018195357 | 10/2018 |
| WO | WO2019075112 | 4/2019 |

OTHER PUBLICATIONS

Nordly et al. (Incorporation of a synthetic mycobacterial monomycoloyl glycerol analogue stabilizes dimethyldioctadecylammonium liposomes and potentiates their adjuvant effect in vivo. European Journal of Pharmaceutics and Biopharmaceutics. 2011. vol. 77, pp. 89-98) (Year: 2011).*

Korsholm et al. (Induction of CD8+ T-cell responses against subunit antigens by the novel cationic liposomal CAF09 adjuvant. Vaccine. 2014. Vol 32, pp. 3927-3935) (Year: 2014).*

Heuts, J. et al, "Cationic liposomes: a flexible vaccine delivery system for physicochemically diverse antigenic peptides", Pharmaceutical Research, vol. 35(11), pp. 1-9, XP036626815, (Sep. 2018).

Overgaard, N. et al, "Establishing the pig as a large animal model for vaccine development against human cancer", Frontiers in Genetics, vol. 6(286), pp. 1-12, XP002798170, Sep. 2015).

Pedersen, G. et al, "Immunocorrelates of CAF family adjuvants", Seminars in Immunology, vol. 39(2), pp. 4-5, DOI: 10.1016/J.Smim. 2018.10.003, (Apr. 2018).

Sahin, U. et al, "Personalized vaccines for cancer immunotherapy", Science, vol. 359(6382), pp. 1355-1360, (Mar. 2018).

Hu, Z. et al, "Towards personalized, tumour-specific, therapeutic vaccines for cancer", Nature Reviews Immunology, vol. 18(3), pp. 168-182, (Mar. 2018).

Keskin, D. et al, "Neoantigen vaccine generates intratumoral T cell responses in phase I-beta glioblastoma trial", Nature, vol. 565(7738), pp. 234-239, published online Dec. 2018, (Jan. 2019).

Pedersen, G. et al, "Immunocorrelates of CAF family adjuvants", Seminars in Immunology, vol. 39, pp. 4-13, (Oct. 2018).

Korsholm, K. et al, "Induction of CD8+ T-cell responses against subunit antigens by the novel catatonic liposomal CAF09 adjuvant", Vaccine, vol. 32, pp. 3927-3935, (2014).

Nana H. Overgaard et al, "Low antigen dose formulated in CAF9 adjuvant Favours a cytotoxic T-cell response following intraperitoneal immunication in Gottingen minipigs", Vaccine, 35:5629-5636 (2017).

Sofie Kirial Mork et al, "Dose escalation study of a personalized peptide-based neoantigen vaccine (EVX-01) in patients with metastic melanoma" (J. Immunother Cancer, 12:e008817 (2024).

Hiep Khong et al, "Adjuvants for peptide-based cancer vaccines", Journal for ImmunoTherapy of Cancer, 4:56 (2016).

(Continued)

*Primary Examiner* — Daniel E Kolker

(74) *Attorney, Agent, or Firm* — McHale & Slavin, P.A.

(57) ABSTRACT

Methods of vaccination utilizing a cationic liposomal adjuvant admixed with at least one neoepitope and a solvent. Also provided are unit dosages and compositions for use in the methods.

35 Claims, 12 Drawing Sheets

Figure 2:
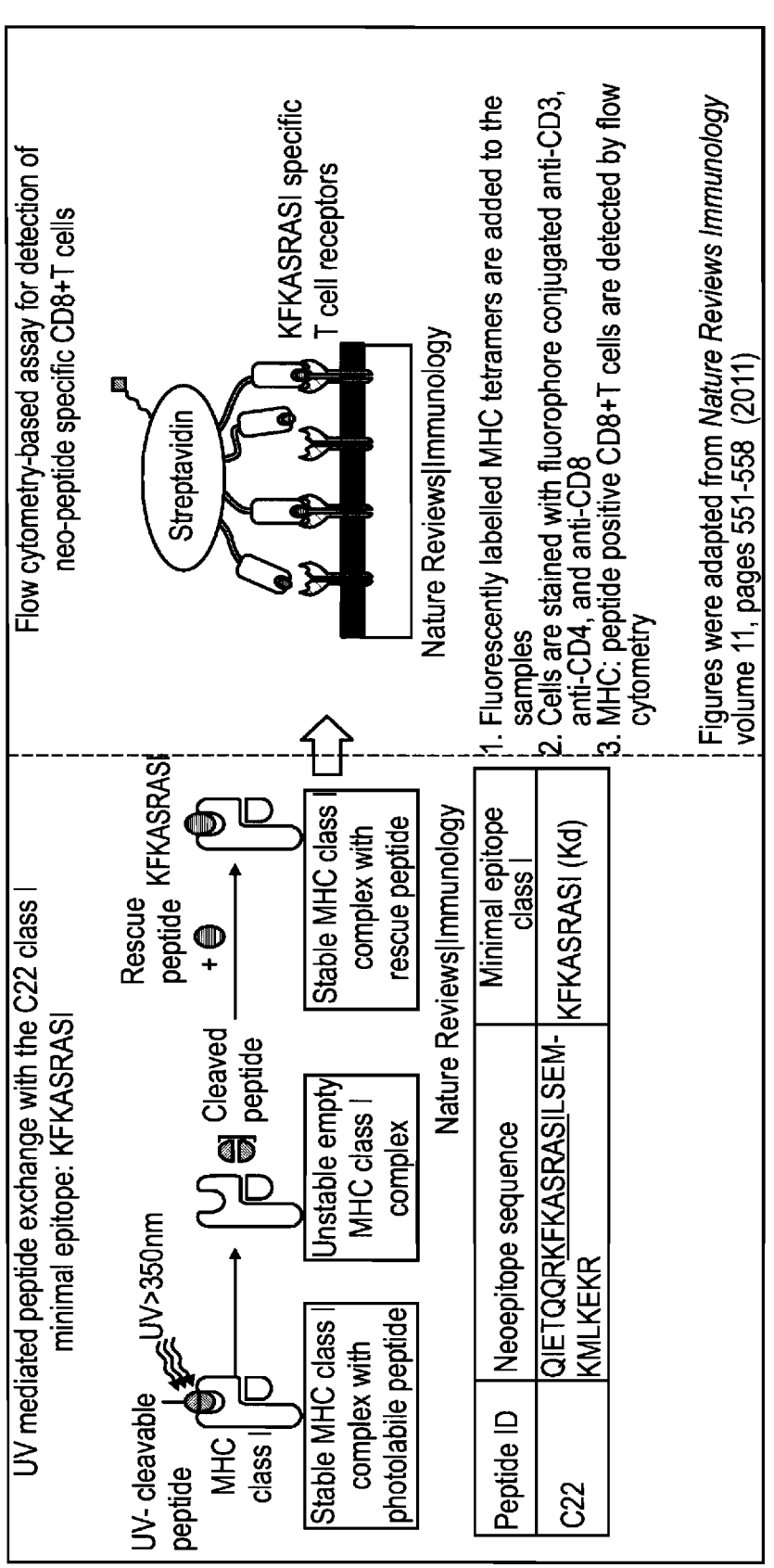

Specification includes a Sequence Listing.

(56)     References Cited

OTHER PUBLICATIONS

Study Identification, "A Phase I Study of the Bcl-XL_42-CAF09b
Vaccine to test Safety and Immunological Effect in Patients with
Prostate Cancer with Lymph Node Metastases" (Jan. 26, 2018).

* cited by examiner

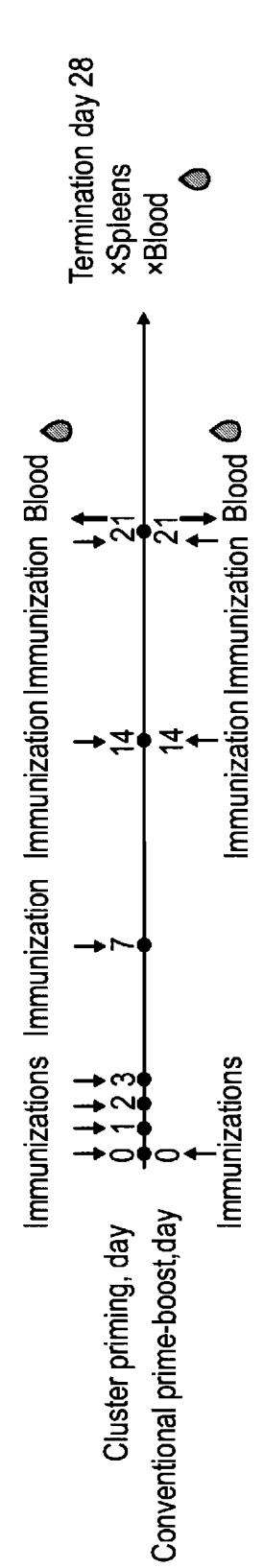

Experimental Design

The mice were either cluster primed with sequential daily immunization or immunized following a conventional prime-boost regiment. Doses of C22 and days of immunization are indicated in the figure. Tumor cells were prepared and inoculated using method outlined in EXP132.

Immunizations Immunization Immunization Immunization Immunization Blood

Cluster priming, day    0 1 2 3    7    14    21    21

Conventional prime-boost,day    0

Immunizations Immunization Immunization Blood

Termination day 28
×Spleens
×Blood

Groups
1. 0.4 µg C22+CAF09b
2. 2.0 µg C22+CAF09b
3. 10.0 µg C22+CAF09b
4. 50.0 µg C22+CAF09b Ip cluster priming
(day 0, 1, 2, 3, 7, 14, 21)

5. 0.4 µg C22+CAF09b
6. 2.0 µg C22+CAF09b
7. 10.0 µg C22+CAF09b
8. 50.0 µg C22+CAF09b

Ip conventional prime-boost
(day 0, 14, 21)

n=4 (6-8 weeks old BALB/c JrJ females were acquired from Janvier Labs)

Read-outs (ROs)
Clinical/animal well being:
Body weight change

Ex vivo:
-Neo-peptide specific CD8+ T cells in whole blood
(day 21 and endpoint)

-Neo_peptide specific CD8+T cells in splenocytes.Only samples from cluster primed groups have been analyzed -T cell activation upon re-stimulation-ongiong Peptides:
C22, doses indicated above CAF09b    200 µg DDA
          40 µg MMG
          40 µg Poly (I:C)

Naive and CAF09b dosed mice from EXP0133 were included as negative controls (these mice were from the same batch)

Fig. 1

SEQUENCE LISTING

<160> NUMBER OF SEQ ID NOS: 23

<210> SEQ ID NO 1
<211> LENGTH: 27
<212> TYPE: PRT
<213> ORGANISM: Mus musculus

<400> SEQUENCE: 1

Gln Ile Glu Thr Gln Gln Arg Lys Phe Lys Ala Ser Arg Ala Ser Ile
1               5                   10                  15

Leu Ser Glu Met Lys Met Leu Lys Glu Lys Arg
            20                  25

<210> SEQ ID NO 2
<211> LENGTH: 9
<212> TYPE: PRT
<213> ORGANISM: Mus musculus

<400> SEQUENCE: 2

Lys Phe Lys Ala Ser Arg Ala Ser Ile
1               5

<210> SEQ ID NO 3
<211> LENGTH: 27
<212> TYPE: PRT
<213> ORGANISM: Homo Sapiens

<400> SEQUENCE: 3

Pro Leu Arg Asp Gly Gly Ala Lys Ile Asp Gly Tyr Ile Ile Ser Tyr
1               5                   10                  15

Arg Glu Glu Glu Gln Pro Ala Asp Arg Trp Thr
            20                  25

<210> SEQ ID NO 4
<211> LENGTH: 22
<212> TYPE: PRT
<213> ORGANISM: Homo Sapiens

<400> SEQUENCE: 4

Ile Leu Val Leu Glu Ser Ser Val Gln Gly Tyr Pro Thr Gln Arg Ala
1               5                   10                  15

Arg Tyr Gln Trp Val Arg
            20

<210> SEQ ID NO 5
<211> LENGTH: 27
<212> TYPE: PRT
<213> ORGANISM: Homo Sapiens

<400> SEQUENCE: 5

Ser Lys Gln Gln Asp Ser Asp Lys Leu Asn Ser Leu Ser Ile Pro Ser
1               5                   10                  15

Val Ser Lys Arg Val Val Leu Gly Asp Ser Val
            20                  25

<210> SEQ ID NO 6
<211> LENGTH: 23
<212> TYPE: PRT
<213> ORGANISM: Homo Sapiens

<400> SEQUENCE: 6

Thr Gly Pro Glu Ser Arg Arg Glu Val Pro Val Tyr Thr Tyr Ser Glu
1               5                   10                  15

```
Pro Arg Gln Glu Val Pro Met
            20

<210> SEQ ID NO 7
<211> LENGTH: 20
<212> TYPE: PRT
<213> ORGANISM: Homo Sapiens

<400> SEQUENCE: 7

Lys Val Gly Asn Asn Ser Ser His Phe Leu Gln Pro Asn Leu Arg Gly
1               5                   10                  15

Pro Leu Phe Leu
            20

<210> SEQ ID NO 8
<211> LENGTH: 25
<212> TYPE: PRT
<213> ORGANISM: Homo Sapiens

<400> SEQUENCE: 8

Trp Ser Ser Ser Arg Arg Ser Arg Ser Ser Tyr Thr His Ser Leu Asn
1               5                   10                  15

Arg Thr Gly Phe Tyr Arg His Ser Gly
            20                  25

<210> SEQ ID NO 9
<211> LENGTH: 27
<212> TYPE: PRT
<213> ORGANISM: Homo Sapiens

<400> SEQUENCE: 9

His Gln Pro Glu Ala Ile Glu Glu Phe Pro Val Pro Ala Phe His His
1               5                   10                  15

Pro Val Phe Gln Gln Glu Ser Phe Thr Arg Gln
            20                  25

<210> SEQ ID NO 10
<211> LENGTH: 19
<212> TYPE: PRT
<213> ORGANISM: Homo Sapiens

<400> SEQUENCE: 10

Phe Val Thr Glu Leu Glu Leu Phe Glu Val Gln Pro Leu Ala Ser Gly
1               5                   10                  15

Asp Tyr Ser

<210> SEQ ID NO 11
<211> LENGTH: 27
<212> TYPE: PRT
<213> ORGANISM: Homo Sapiens

<400> SEQUENCE: 11

Asp Arg Glu Lys Ile Tyr Gln Trp Ile Asn Glu Leu Ser Gly Pro Glu
1               5                   10                  15

Thr Arg Glu Asn Ala Leu Leu Glu Leu Ser Lys
            20                  25

<210> SEQ ID NO 12
<211> LENGTH: 25
<212> TYPE: PRT
<213> ORGANISM: Homo Sapiens
```

-continued

```
<400> SEQUENCE: 12

Asp Lys Ile Gly Pro Val Asp His Ile Glu Phe Phe Ser Gly Pro Glu
1               5                   10                  15

Phe Lys Lys Thr Leu Ala Ser Lys Thr
            20                  25

<210> SEQ ID NO 13
<211> LENGTH: 25
<212> TYPE: PRT
<213> ORGANISM: Homo Sapiens

<400> SEQUENCE: 13

Val Lys Thr Arg Met Gln Ser Leu Gln Pro Asp Leu Ala Ala Arg Tyr
1               5                   10                  15

Arg Asn Val Leu Glu Ala Leu Trp Arg
            20                  25

<210> SEQ ID NO 14
<211> LENGTH: 27
<212> TYPE: PRT
<213> ORGANISM: Homo Sapiens

<400> SEQUENCE: 14

His Arg Phe Glu Arg Glu Asp Val Asp Asp Ile Lys Val Tyr Ser Pro
1               5                   10                  15

Tyr Glu Ile Ser Ile Arg Gln Arg Phe Ile Gly
            20                  25

<210> SEQ ID NO 15
<211> LENGTH: 27
<212> TYPE: PRT
<213> ORGANISM: Homo Sapiens

<400> SEQUENCE: 15

Leu Leu Ala Ser Gly Arg Ala Pro Arg Arg Ala Ser Ser Ala Leu Pro
1               5                   10                  15

Arg Asn Thr Val Val Leu Phe Val Pro Gln Gln
            20                  25

<210> SEQ ID NO 16
<211> LENGTH: 27
<212> TYPE: PRT
<213> ORGANISM: Homo Sapiens

<400> SEQUENCE: 16

Tyr Val Lys Ala Glu Lys Asn Val Pro Asp Leu Lys Ser Ile Tyr Asn
1               5                   10                  15

Asn Val Leu Gln Leu Ile Lys Val Asn Phe Ser
            20                  25

<210> SEQ ID NO 17
<211> LENGTH: 27
<212> TYPE: PRT
<213> ORGANISM: Artificial sequence
<220> FEATURE:
<223> OTHER INFORMATION: Model peptide

<400> SEQUENCE: 17

Gln Ile Glu Thr Gln Cys Arg Lys Phe Lys Ala Ser Arg Ala Ser Ile
1               5                   10                  15

Leu Ser Glu Met Lys Met Leu Lys Glu Lys Arg
            20                  25
```

-continued

```
<210> SEQ ID NO 18
<211> LENGTH: 21
<212> TYPE: PRT
<213> ORGANISM: Artificial sequence
<220> FEATURE:
<223> OTHER INFORMATION: Model peptide truncate

<400> SEQUENCE: 18

Arg Lys Phe Lys Ala Ser Arg Ala Ser Ile Leu Ser Glu Met Lys Met
1               5                   10                  15

Leu Lys Glu Lys Arg
            20

<210> SEQ ID NO 19
<211> LENGTH: 27
<212> TYPE: PRT
<213> ORGANISM: Artificial sequence
<220> FEATURE:
<223> OTHER INFORMATION: Model peptide

<400> SEQUENCE: 19

Gln Ile Glu Thr Gln Gln Arg Lys Phe Lys Ala Ser Arg Ala Ser Ile
1               5                   10                  15

Leu Ser Glu Met Lys Met Leu Lys Glu Lys Arg
            20                  25

<210> SEQ ID NO 20
<211> LENGTH: 26
<212> TYPE: PRT
<213> ORGANISM: Artificial sequence
<220> FEATURE:
<223> OTHER INFORMATION: Model peptide truncate

<400> SEQUENCE: 20

Ile Glu Thr Gln Gln Arg Lys Phe Lys Ala Ser Arg Ala Ser Ile Leu
1               5                   10                  15

Ser Glu Met Lys Met Leu Lys Glu Lys Arg
            20                  25

<210> SEQ ID NO 21
<211> LENGTH: 27
<212> TYPE: PRT
<213> ORGANISM: Artificial sequence
<220> FEATURE:
<223> OTHER INFORMATION: Model peptide

<400> SEQUENCE: 21

Asn Ile Glu Thr Gln Gln Arg Lys Phe Lys Ala Ser Arg Ala Ser Ile
1               5                   10                  15

Leu Ser Glu Met Lys Met Leu Lys Glu Lys Arg
            20                  25

<210> SEQ ID NO 22
<211> LENGTH: 27
<212> TYPE: PRT
<213> ORGANISM: Artificial sequence
<220> FEATURE:
<223> OTHER INFORMATION: Model peptide

<400> SEQUENCE: 22

Asp Gly Glu Thr Gln Gln Arg Lys Phe Lys Ala Ser Arg Ala Ser Ile
1               5                   10                  15

Leu Ser Glu Met Lys Met Leu Lys Glu Lys Arg
```

-continued

```
            20                  25

<210> SEQ ID NO 23
<211> LENGTH: 26
<212> TYPE: PRT
<213> ORGANISM: Artificial sequence
<220> FEATURE:
<223> OTHER INFORMATION: Model peptide truncate

<400> SEQUENCE: 23

Gly Glu Thr Gln Gln Arg Lys Phe Lys Ala Ser Arg Ala Ser Ile Leu
1               5                  10                  15

Ser Glu Met Lys Met Leu Lys Glu Lys Arg
            20                  25
```

VACCINES TARGETING NEOEPITOPES

CROSS REFERENCE TO RELATED APPLICATIONS

This is a national stage filing in accordance with 35 U.S.C. § 371 of PCT/EP2020/050058, filed Jan. 3, 2020, which claims the benefit of the priority of European Patent Application No. 19207238.7, filed Nov. 5, 2019 and European Patent Application No. 19150200.4, filed Jan. 3, 2019, the contents of each are incorporated herein by reference.

FIELD OF THE INVENTION

The present invention relates to the field of immunotherapy. In particular, the present invention relates to therapeutic immunization technologies for treatment of neoplastic diseases.

BACKGROUND OF THE INVENTION

Treatment of malignant neoplasms in patients has traditionally focussed on eradication/removal of the malignant tissue via surgery, radiotherapy, and/or chemotherapy using cytotoxic drugs in dosage regimens that aim at preferential killing of malignant cells over killing of non-malignant cells.

In addition to the use of cytotoxic drugs, more recent approaches have focussed on targeting of specific biologic markers in the cancer cells in order to reduce systemic adverse effects exerted by classical chemotherapy. Monoclonal antibody therapy targeting cancer associated antigens has proven quite effective in prolonging life expectance in a number of malignancies. While being successful drugs, monoclonal antibodies that target cancer associated antigens or antigen can by their nature only be developed to target expression products that are known and appear in a plurality of patients, meaning that the vast majority of cancer specific antigens cannot be addressed by this type of therapy, because a large number of cancer specific antigens only appear in tumours from one single patient, cf. below.

As early as in the late 1950'ies the theory of immunosurveillance proposed by Burnet and Thomas suggested that lymphocytes recognizes and eliminates autologous cells—including cancer cells—that exhibit altered antigenic determinants, and it is today generally accepted that the immune system inhibits carcinogenesis to a high degree. Nevertheless, immunosurveillance is not 100% effective and it is a continuing task to device cancer therapies where the immune system's ability to eradicate cancer cells is sought improved/stimulated.

One approach has been to induce immunity against cancer-associated antigens, but even though this approach has the potential of being promising, it suffers the same drawback as antibody therapy that only a limited number of antigens can be addressed.

Many if not all tumours express mutations. These mutations potentially create new targetable antigens (neo-antigens), which are potentially useful in specific T cell immunotherapy if it is possible to identify the neo-antigens and their antigenic determinants within a clinically relevant time frame. Since it with current technology is possible to fully sequence the genome of cells and to analyse for existence of altered or new expression products, it is possible to design personalized vaccines based neo-antigens. However, attempts at providing satisfactory clinical end-points has as today failed.

There is hence an existing need for provision of anti-cancer vaccines that can effectively target neo-antigens and induce clinically significant immune responses in the vaccinated individuals.

OBJECT OF THE INVENTION

It is an object of embodiments of the invention to provide methods for induction of therapeutically effective immune responses against neo-antigens that comprise neo-epitopes. It is a further object to provide compositions comprising neo-epitope material that can be used for cancer immunotherapy.

SUMMARY OF THE INVENTION

It has been found by the present inventor(s) that formulation of neo-peptides with certain cationic liposomal adjuvants and administration of such formulations using a relatively high dosage of the neo-peptides provide for improved immune responses in vaccinated individuals. In turn, this is believed to provide for an improvement in cancer immunotherapy of cancers characterized by expression of neo-epitope containing expression products.

So, in a first aspect the present invention relates to a method for treatment of a neoplasm, such as a malignant neoplasm, in a mammalian patient, wherein the neoplasm exhibits T-cell epitopes (neo-epitopes) that are not exhibited by non-neoplastic cells in the patient, the method comprising administering an immunogenically effective amount of a liposomal composition comprising 1) at least one peptide (neo-peptide), which comprises an amino acid sequence of a neo-epitope of the patient's neoplastic cells, 2) a solvent, and 3) a cationic liposomal adjuvant.

A second aspect of the invention relates to a unit dose of an immunogenic composition, said unit dose comprising an immunogenically effective amount of at least one peptide (neo-peptide), which comprises an amino acid sequence of a neo-epitope of a patient's neoplastic cells, a cationic liposomal adjuvant, and a solvent.

A third aspect of the invention relates to a liposomal composition with the characteristics of the liposomal composition administered as part of the first aspect of the invention.

Related aspects pertain to the unit dose of the second aspect and the composition of the third aspect for use in therapy and prophylactic therapy, in particular for use in the method of the first aspect of the invention.

LEGENDS TO THE FIGURE

FIG. 1: Experimental design of immunization study in Example 1.

Mice were either cluster primed with sequential daily immunization or immunized following a conventional prime-boost regiment. Doses of C22 and days of immunization are indicated in the figure. Ip: intraperitoneal.

FIG. 2: Overview of MHC I multimer assay.

MHC class I molecules were produced and loaded with a stabilizing peptide that was exchanged with the C22 minimal epitope KFKASRASI by exposing the molecules to UV light. The MHC I molecules were multimerized by coupling to fluorescently labelled Streptavidin. To identify neo-peptide positive CD8+ T cells, the blood cells were co-stained with the multimers and fluorophore conjugated anti-CD3, anti-CD4 and anti-CD8 antibodies. Samples were then analyzed by flow cytometry and the fraction of MHC: C22 positive CD8+ was calculated.

Figures 3A, 3B:
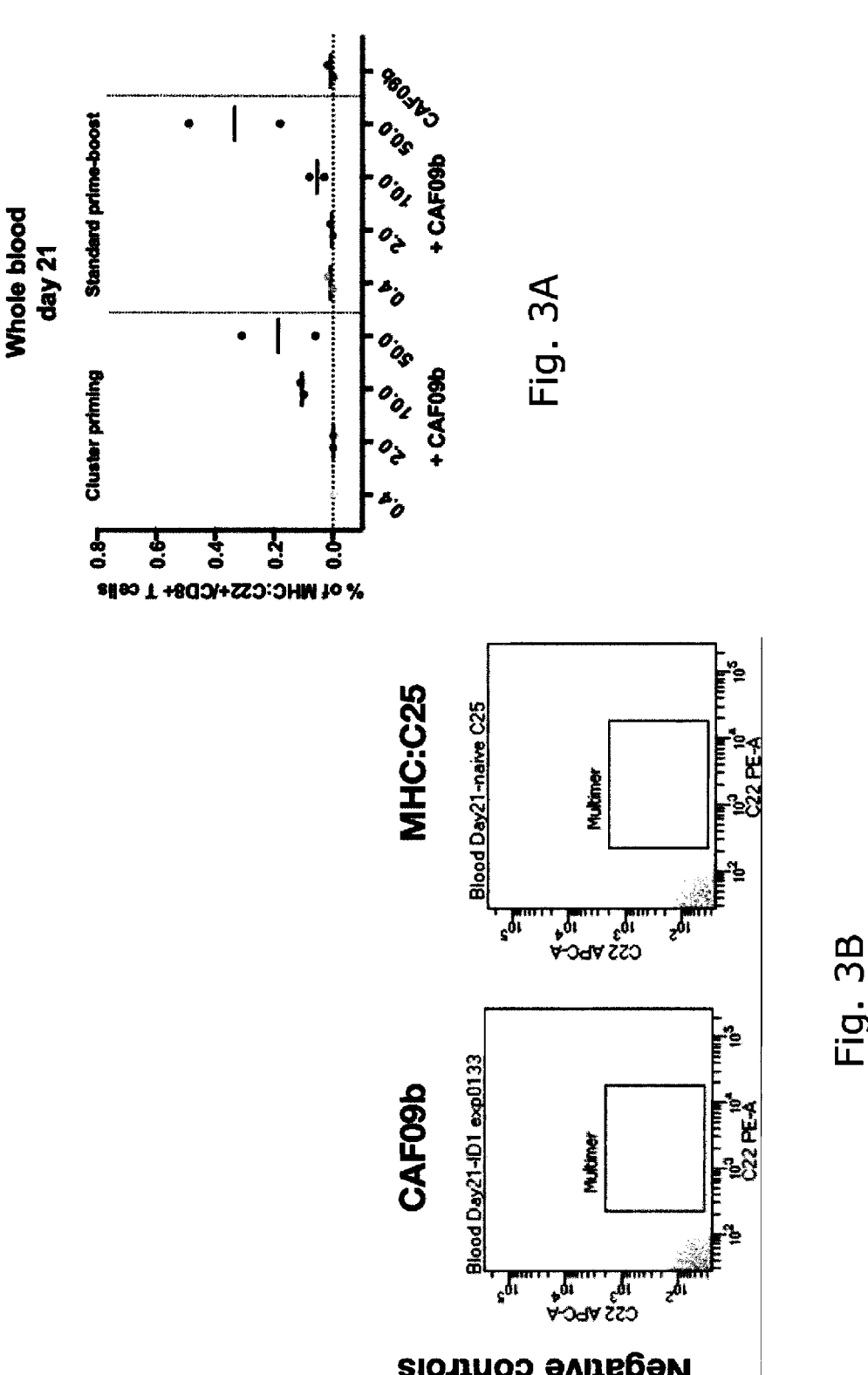
Figure 3C:
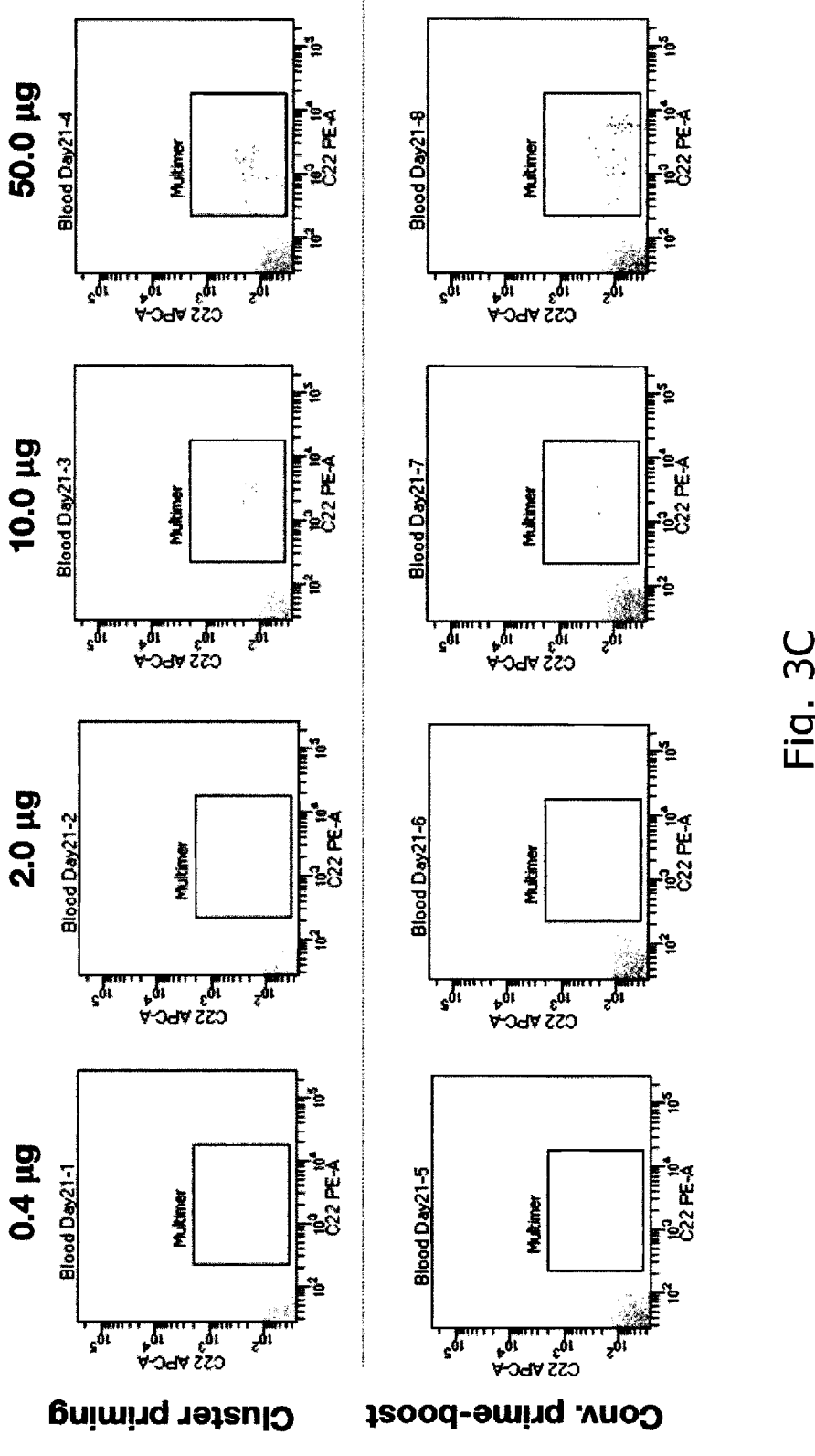

FIG. 3: Detection of neo-peptide specific CD8+ T cells in whole blood at day 21.

FIG. 3A depicts the percentage of multimer positive CD8+ in blood from two mice in each group 21 days after first immunization. Circulating C22 specific CD8+ T cells were detected in mice immunized with 10.0 and 50.0 μg C22 formulated with CAF09b, irrespective of immunization schedule. Only blood from two mice from each group was stained.

In FIGS. 3B and C, representative plots from the flow cytometric analysis are shown, with the controls in FIG. 3B.

FIG. 4: Detection of neo-peptide specific CD8+ T cells in whole blood at endpoint day 28.

Figures 4A, 4B:
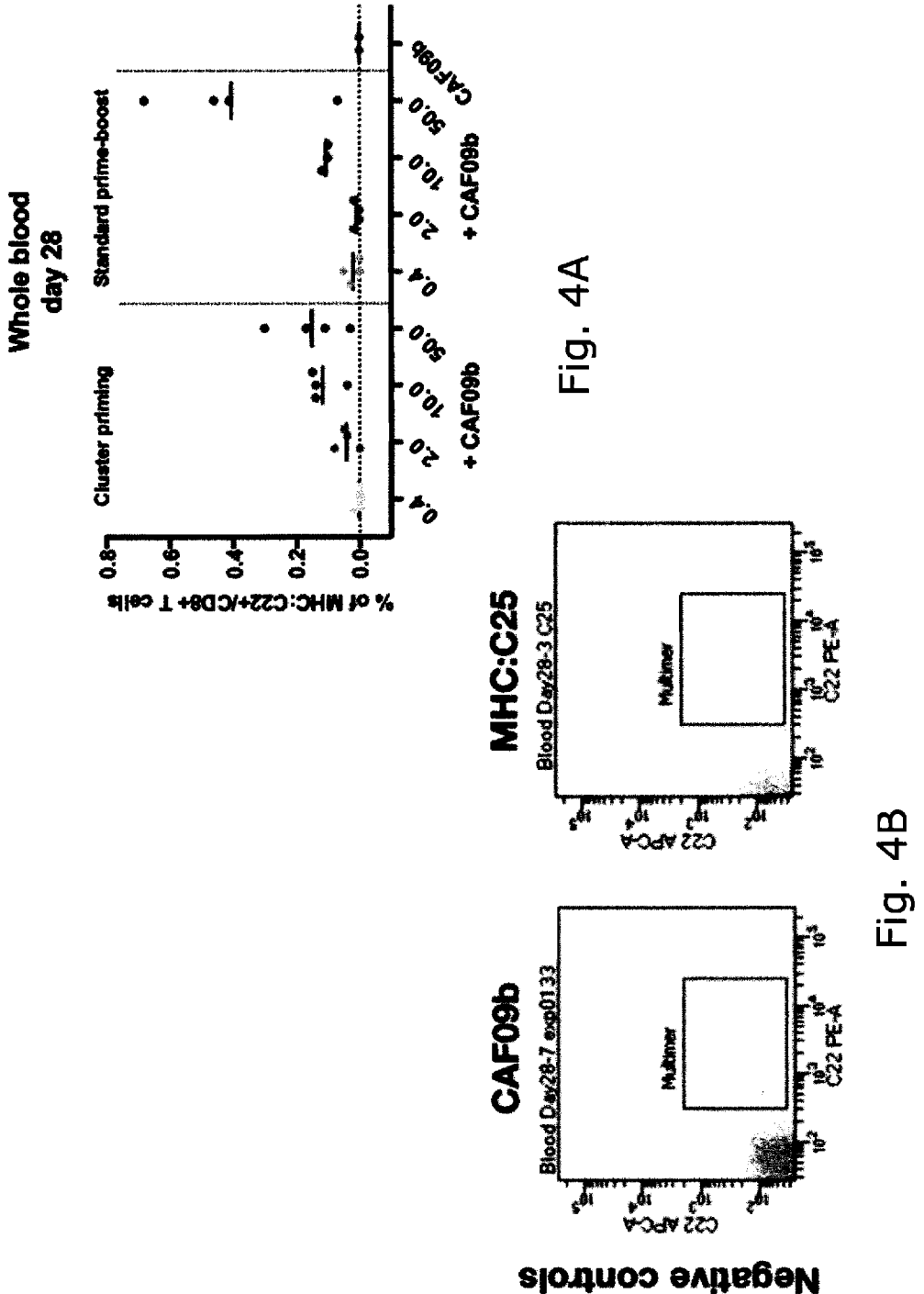
Figure 4C:
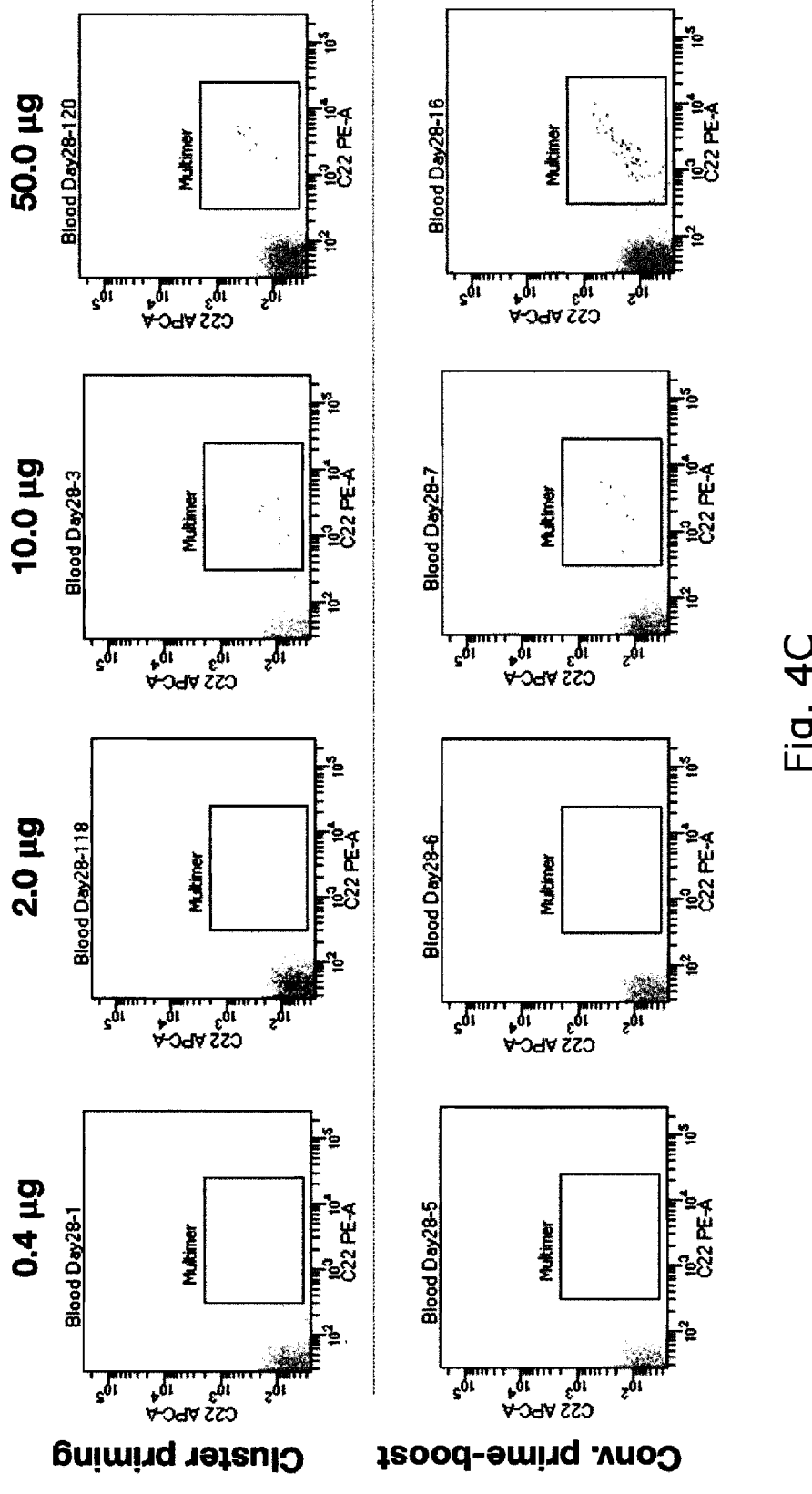

FIG. 4A depicts the percentage of multimer positive CD8+ in blood from two mice in each group 28 days post first immunization. Circulating C22 specific CD8+ T cells were detected in mice immunized with 10.0 and 50.0 μg C22 formulated with CAF09b, irrespective of immunization schedule. A small increase in the fraction was also seen in mice cluster primed with 2.0 μg C22. In FIGS. 4B and 4C, representative plots from the flow cytometric analysis are shown with the controls shown in FIG. 4B.

FIG. 5: Detection of neo-peptide specific splenic CD8+ T cells.

Figures 5A, 5B:
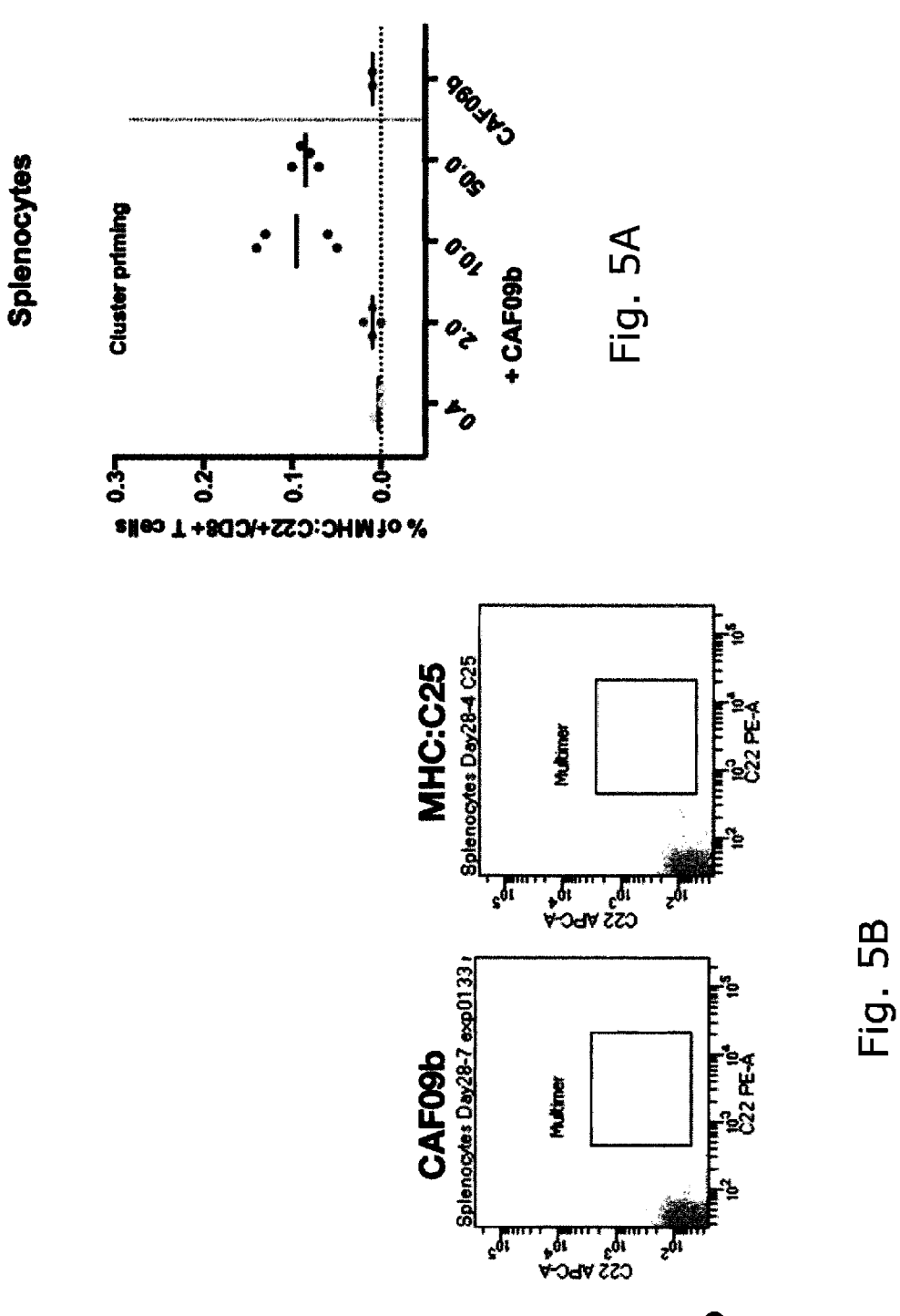
Figure 5C:
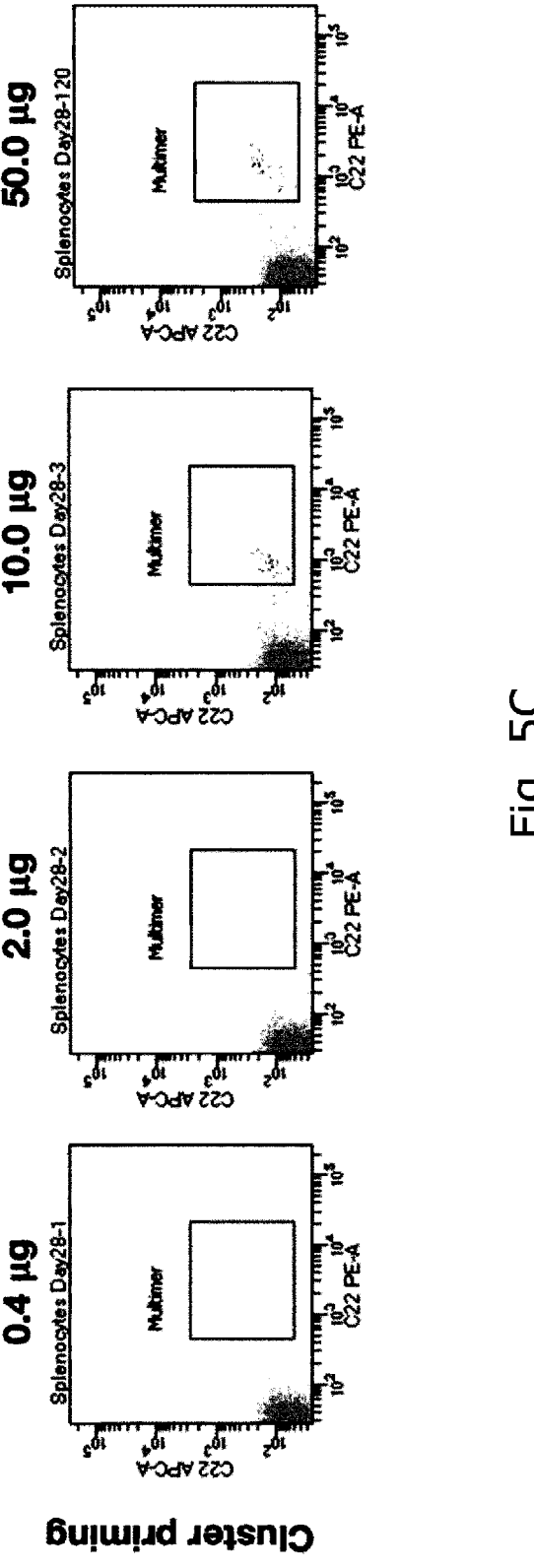

FIG. 5A depicts the percentage of multimer positive splenic CD8+ T cells from the cluster primed mice at endpoint (28 days after first immunization). C22 specific CD8+ T cells were detected in mice immunized with 10.0 and 50.0 μg C22 formulated with CAF09b. In FIGS. 5B and 5C representative plots from the flow cytometric analysis are shown, with the negative controls shown in FIG. 5B.

Figure 6A:
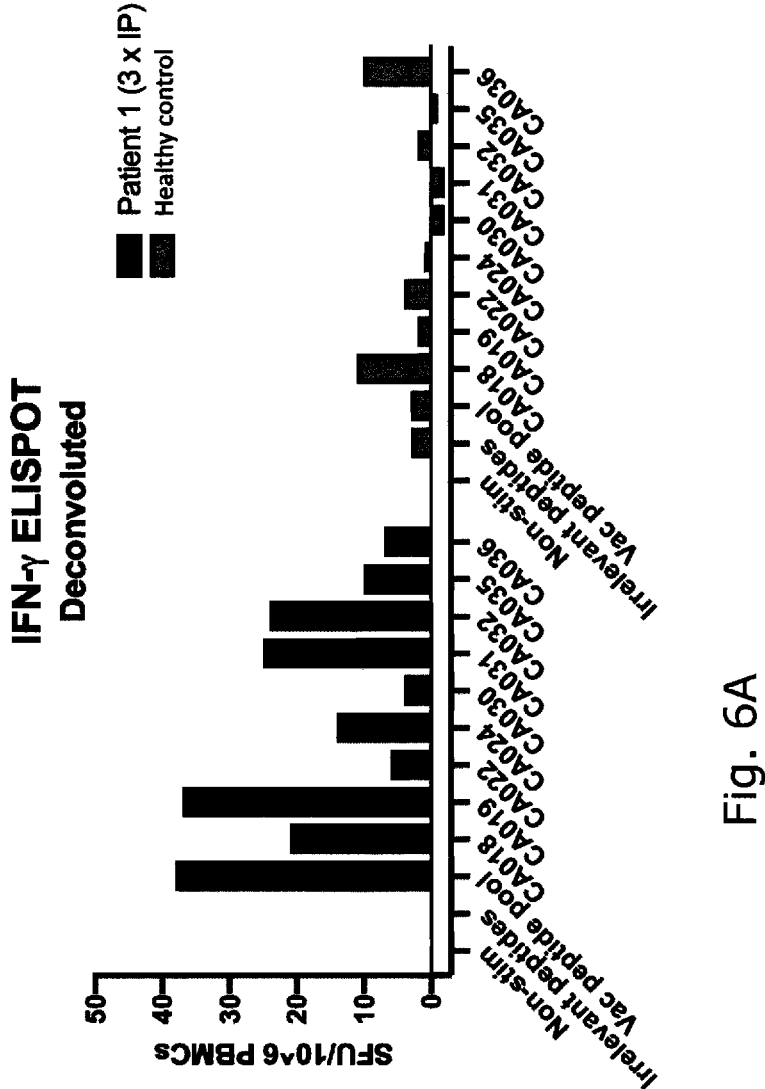
Figure 6B:
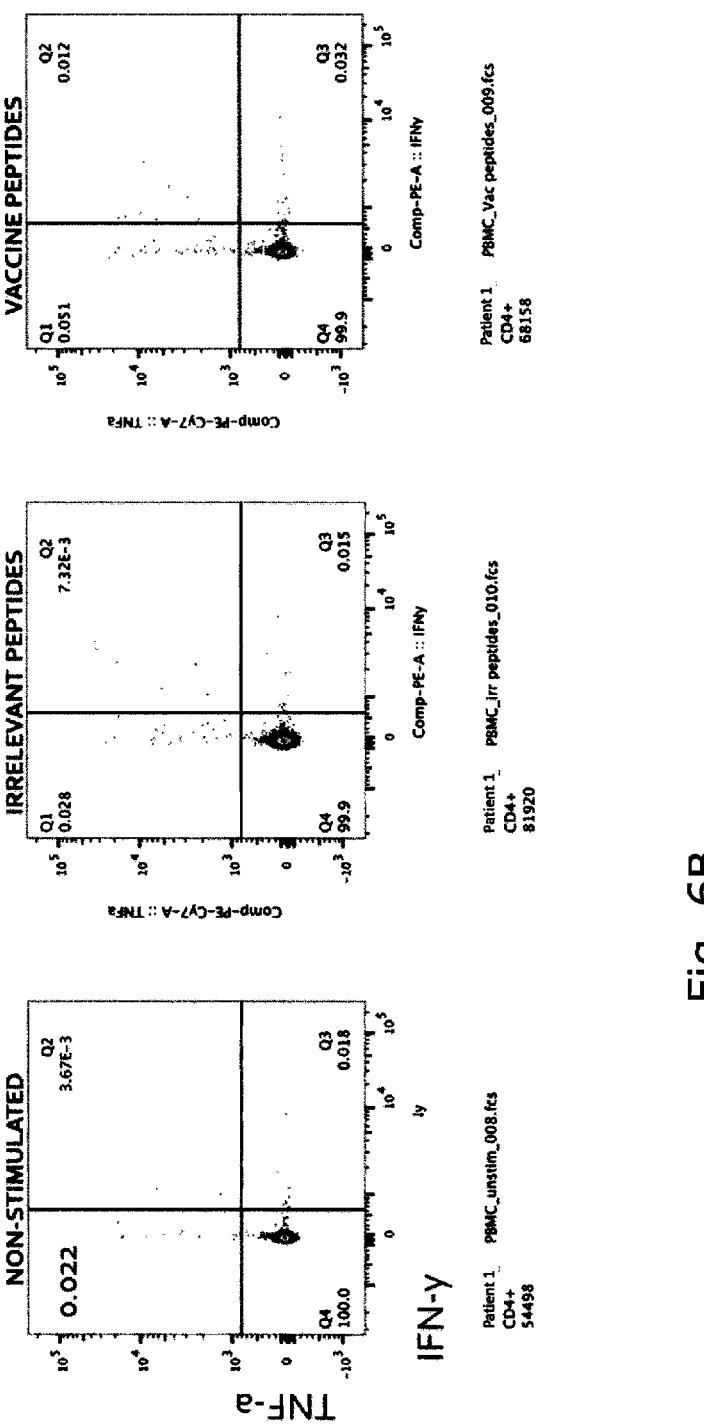

FIG. 6: Data from immunization of "patient 1".

A: ELISPOT data showing IFN-γ release from post-immunized PBMCs stimulated with the 9 peptides of the vaccine containing neo-epitope. The Healthy control group are data from a parallel experiment on PBMCs from a control donor. CA019 was administered in double dosage.

B: Flowcytometric data from PBMCs obtained after intraperitoneal immunizations. The left hand panel shows TNF-α and IFN-γ release from non stimulated PBMCs, the middle panel shows TNF-α and IFN-γ release from PBMCs stimulated with irrelevant peptides, and the right hand panel shows TNF-α and IFN-γ release from PBMCs stimulated with the 9 peptides of the vaccine.

Figure 7A:
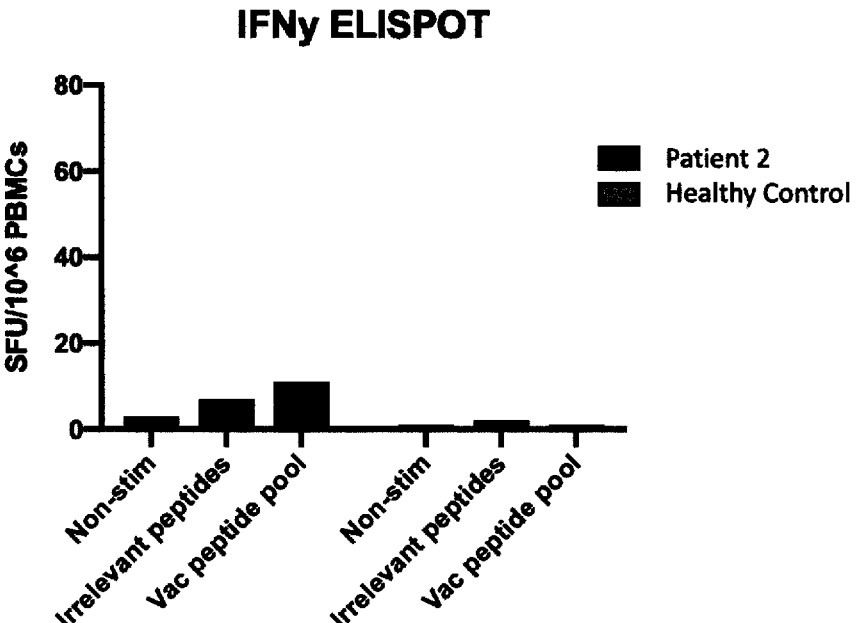
Figure 7B:
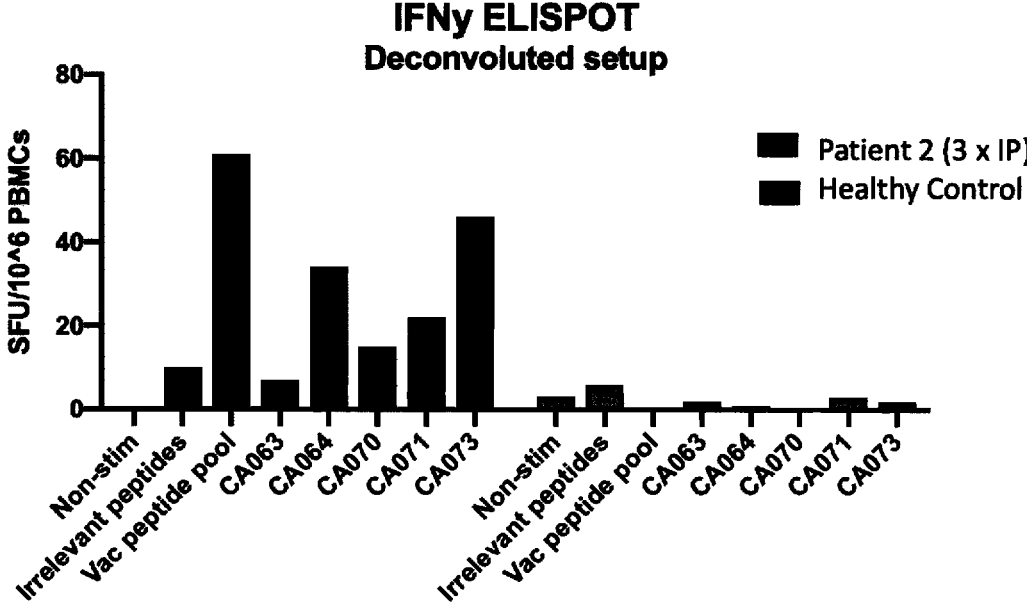
Figures 7C, 7D:
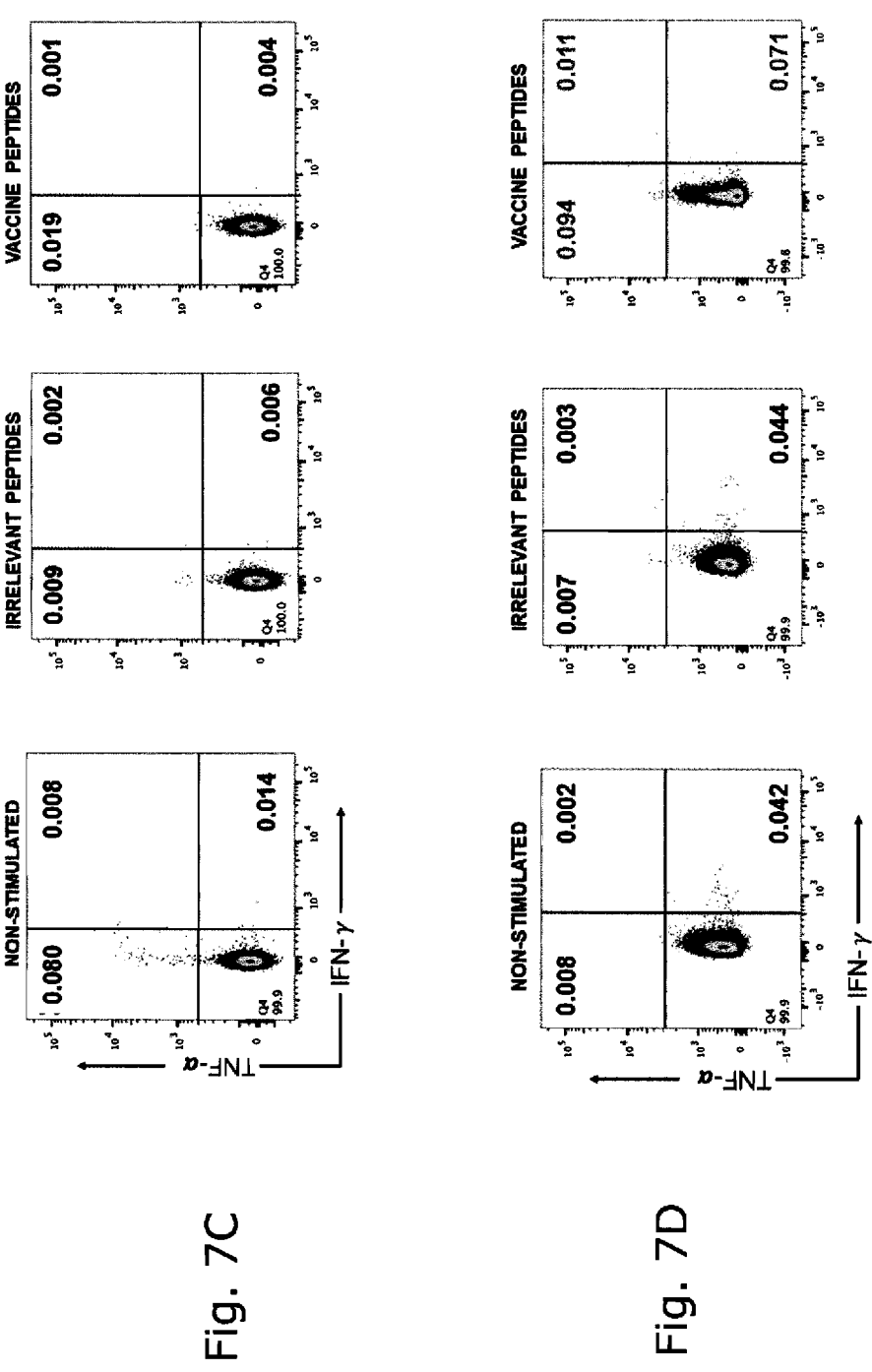

FIG. 7: Data from immunization of "patient 2".

A: ELISPOT data showing IFN-γ release from PBMCs obtained prior to immunization and stimulated with the 5 peptides of the neo-epitope containing vaccine. Healthy control are data from a parallel experiment on PBMCs from a control donor.

B: ELISPOT data showing IFN-γ release from PBMCs obtained after intraperitoneal immunizations and after stimulation with the 5 peptides of the neo-epitope containing vaccine. Healthy control group are data from a parallel experiment on PBMCs from a control donor.

C: Flowcytometric data of TNF-α and IFN-γ release from PBMCs obtained prior to immunization. The left hand panel shows release from non stimulated PBMCs, the middle panel shows release from PBMCs stimulated with irrelevant peptides, and the right hand panel shows release from PBMCs stimulated with the 5 peptides of the vaccine.

D: Flowcytometric data of TNF-α and IFN-γ release from PBMCs obtained after intraperitoneal immunizations. The left hand panel shows release from non stimulated PBMCs, the middle panel shows release from PBMCs stimulated with irrelevant peptides, and the right hand panel shows release from PBMCs stimulated with the 5 peptides of the vaccine.

DETAILED DISCLOSURE OF THE INVENTION

Definitions

A "cancer specific" antigen, is an antigen, which does not appear as an expression product in an individual's non-malignant somatic cells, but which appears as an expression product in cancer cells in the individual. This is in contrast to "cancer-associated" antigens, which also appear—albeit at low abundance—in normal somatic cells, but are found in higher levels in at least some tumour cells.

The term "adjuvant" has its usual meaning in the art of vaccine technology, i.e. a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combined vaccination with immunogen and adjuvant induces an immune response against the immunogen which is stronger than that induced by the immunogen alone.

"CAF09" (Cationic Adjuvant Formulation 09) is an immunologic adjuvant liposome formulation, which comprises the quaternary ammonium surfactant N,N-dimethyl-N,N-dioctadecylammonium (DDA), a synthetic 3-hydroxy-2-tetradecyl-octadecanoic acid-2,3-dihydroxypropyl ester (monomycolyl glycerol, "MMG"), which acts as a ligand for C-type lectin receptors (CLRs), and Polyinosinic-polycytidylic acid (sodium salt) ("poly-IC" or "poly(I:C)"), which acts as a ligand for toll-like receptors ("TLRs"). A number of CAF family adjuvants, including CAF09, is disclosed in detail in US 2014/0112979 and in US 2016/0228528. The relative amounts (w:w:w) of DDA:MMG:Poly(I:C) are 5:1:1.

"CAF09b" is a version of CAF09 with the relative amount of poly(I:C) reduced to about ¼ of the amount disclosed in US 2014/0112979: in CAF09, the relative amounts (w:w:w) of DDA:MMG:poly(I:C) are thus 20:4:1 with a typical human dose containing 625 μg DDA, 125 μg DDA, and 31.25 μg poly(I:C), respectively.

A "neo-epitope" is an antigenic determinant (typically an MHC Class I or II restricted epitope), which does not exist as an expression product from normal somatic cells in an individual due to the lack of a gene encoding the neo-epitope, but which exists as an expression product in mutated cells (such as cancer cells) in the same individual. As a consequence, a neo-epitope is from an immunological viewpoint truly non-self in spite of its autologous origin and it can therefore be characterized as a tumour specific antigen in the individual, where it constitutes an expression product. Being non-self, a neo-epitope has the potential of being able to elicit a specific adaptive immune response in the individual, where the elicited immune response is specific for antigens and cells that harbour the neo-epitope. Neo-epitopes are on the other hand specific for an individual as the chances that the same neo-epitope will be an expression product in other individuals is minimal. Several features thus contrast a neo-epitope from e.g. epitopes of tumour specific antigens: the latter will typically be found in a plurality of cancers of the same type (as they can be expression products from activated oncogenes) and/or they will be present—albeit in minor amounts—in non-malignant cells because of over-expression of the relevant gene(s) in cancer cells.

A "neo-peptide" is a peptide (i.e. a polyamino acid of up to about 50 amino acid residues), which includes within its sequence a neo-epitope as defined herein. A neo-peptide is typically "native", i.e. the entire amino acid sequence of the neo-peptide constitutes a fragment of an expression product that can be isolated from the individual, but a neo-peptide can also be "artificial", meaning that it is constituted by the sequence of a neo-epitope and 1 or 2 appended amino acid sequences of which at least one is not naturally associated with the neo-epitope. In the latter case the appended amino acid sequences may simply act as carriers of the neo-epitope, or may even improve the immunogenicity of the neo-epitope (e.g. by facilitating processing of the neo-peptide by antigen-presenting cells, improving biologic half-life of the neo-peptide, or modifying solubility).

The term "amino acid sequence" is the order in which amino acid residues, connected by peptide bonds, lie in the chain in peptides and proteins. Sequences are conventionally listed in the N to C terminal direction.

"An immunogenic carrier" is a molecule or moiety to which an immunogen or a hapten can be coupled in order to enhance or enable the elicitation of an immune response against the immunogen/hapten. Immunogenic carriers are in classical cases relatively large molecules (such as tetanus toxoid, KLH, diphtheria toxoid etc.) which can be fused or conjugated to an immunogen/hapten, which is not sufficiently immunogenic in its own right—typically, the immunogenic carrier is capable of eliciting a strong T-helper lymphocyte response against the combined substance constituted by the immunogen and the immunogenic carrier, and this in turn provides for improved responses against the immunogen by B-lymphocytes and cytotoxic lymphocytes. More recently, the large carrier molecules have to a certain extent been substituted by so-called promiscuous T-helper epitopes, i.e. shorter peptides that are recognized by a large fraction of HLA haplotypes in a population, and which elicit T-helper lymphocyte responses.

A "T-helper lymphocyte response" is an immune response elicited on the basis of a peptide, which is able to bind to an MHC class II molecule (e.g. an HLA class II molecule) in an antigen-presenting cell and which stimulates T-helper lymphocytes in an animal species as a consequence of T-cell receptor recognition of the complex between the peptide and the MHC Class II molecule presenting the peptide.

An "immunogen" is a substance of matter which is capable of inducing an adaptive immune response in a host, whose immune system is confronted with the immunogen. As such, immunogens are a subset of the larger genus "antigens", which are substances that can be recognized specifically by the immune system (e.g. when bound by antibodies or, alternatively, when fragments of the are antigens bound to MHC molecules are being recognized by T-cell receptors) but which are not necessarily capable of inducing immunity—an antigen is, however, always capable of eliciting immunity, meaning that a host that has an established memory immunity against the antigen will mount a specific immune response against the antigen.

A "hapten" is a small molecule, which can neither induce or elicit an immune response, but if conjugated to an immunogenic carrier, antibodies or TCRs that recognize the hapten can be induced upon confrontation of the immune system with the hapten carrier conjugate.

An "adaptive immune response" is an immune response in response to confrontation with an antigen or immunogen, where the immune response is specific for antigenic determinants of the antigen/immunogen—examples of adaptive immune responses are induction of antigen specific antibody production or antigen specific induction/activation of T helper lymphocytes or cytotoxic lymphocytes.

A "protective, adaptive immune response" is an antigen-specific immune response induced in a subject as a reaction to immunization (artificial or natural) with an antigen, where the immune response is capable of protecting the subject against subsequent challenges with the antigen or a pathology-related agent that includes the antigen. Typically, prophylactic vaccination aims at establishing a protective adaptive immune response against one or several pathogens.

"Stimulation of the immune system" means that a substance or composition of matter exhibits a general, non-specific immunostimulatory effect. A number of adjuvants and putative adjuvants (such as certain cytokines) share the ability to stimulate the immune system. The result of using an immunostimulating agent is an increased "alertness" of the immune system meaning that simultaneous or subsequent immunization with an immunogen induces a significantly more effective immune response compared to isolated use of the immunogen.

The term "polypeptide" is in the present context intended to mean both short peptides of from 2 to 50 amino acid residues, oligopeptides of from 50 to 100 amino acid residues, and polypeptides of more than 100 amino acid residues. Furthermore, the term is also intended to include proteins, i.e. functional biomolecules comprising at least one polypeptide; when comprising at least two polypeptides, these may form complexes, be covalently linked, or may be non-covalently linked. The polypeptide (s) in a protein can be glycosylated and/or lipidated and/or comprise prosthetic groups.

Specific Embodiments of the Invention

Treatment Methods of the Invention—First Aspect

The method of the first aspect of the invention generally relates to induction of immunity and as such also entails methods that relate to treatment, prophylaxis and amelioration of disease; in particular, the method relates to treatment and amelioration of cancer. That is, the first aspect of the invention relates generally to a method for treatment of a neoplastic disease, such as a malignant neoplastic disease, in a mammalian patient, wherein the cells of the neoplasm exhibits T-cell epitopes (neo-epitopes) that are not exhibited by non-neoplastic cells in the patient, the method comprising administering an immunogenically effective amount of a liposomal composition comprising 1) at least one peptide (neo-peptide), which comprises an amino acid sequence of a neo-epitope of the patient's neoplastic cells, 2) a solvent, and 3) a cationic liposomal adjuvant.

A number of cationic liposomal adjuvants are known. Of these, those preferred according to the present invention are part of a line of immunologic adjuvants developed at Statens Serum Institute in Denmark and known as CAFs (Cationic Adjuvant Formulations); a recent review describes the general features of the CAF line of adjuvants: Pedersen G K et al. (2018), Semin Immunol 39:4-13. doi: 10.1016/j.smim.2018.10.003. All the CAFs are characterized by comprising the surfactant dimethyldioctadecylammonium (DDA) and most exist as liposomal formulations (CAF01, CAF04, CAF05, CAF06, CAF09, CAF10, and CAF11) whereas a few recently developed CAFs are in the form of emulsions (CAF19 and CAF24) comprising an oil (squalene).

Particularly interesting cationic liposomal adjuvants are according to the invention those that comprise or consist of DDA, poly(I:C), and MMG (including synthetic analogues of MMG, such as 3-hydroxy-2-tetradecyl-octadecanoic acid-2,3-dihydroxypropyl ester). In other words, these are the CAF09 adjuvants.

In the preferred cationic liposomal adjuvant, the ratio DDA:MMG is 5:1 by (w/w) and the ratio DDA:poly(I:C) is between 5:1 and 20:1 (w/w). For instance, the DDA:MMG: poly(I:C) relative weights can according to the invention be 5:1:1 as is the case for "traditional" CAF09, and the DDA: MMG:poly(I:C) relative weights can be 20:4:1, which is the case for the CAF09b adjuvant.

It is preferred that the neo-peptides are soluble in water, so as to facilitate their formulation in a vaccine. For this purpose, the neo-peptides are carefully selected to fulfil certain solubility criteria prior to their inclusion in a vaccine formulation. For instance, it is preferred that the at least one neo-peptide is water-soluble in the sense that 1.0 mg/ml neo-peptide in 25 mM TRIS pH 7.4 containing 5% (v/v) DMSO provides for an NTU (nephelometric turbidity unit) of at most 50, and that 0.1 mg/ml neo-peptide in 25 mM TRIS pH 7.4 and 0.5% (v/v) DMSO provides for an NTU of at most 25, when the NTU is measured according to the European Pharmacopeia, section 2.2.1.

To be more specific, the neo-peptides are tested in an assay that involves spectrophotometric measurements at 620 nm to determine the degree of opalescence (i.e. turbidity) of a peptide solution in TRIS-buffer at various concentrations, and to calculate from this the corresponding NTU-values (using a calibration curve from reference suspension measurements using a Primary Opalescent Suspension, Fisher Scientific; EPPOS01). This can be used to qualify a given neo-peptide as "soluble" (NTU<25 at 0.1 mg/mL; NTU<50 at 1.0 mg/mL) or "insoluble" (NTU>25 at 0.1 mg/mL; NTU>50 at 1.0 mg/mL). The method is used to determine the solubility of HPLC-purified (>95% purity) linear peptides consisting of natural L-amino acids (typically excluding cysteine residues) formulated as 0.1 mg/ml of each tested peptide in TRIS-buffer (containing 0.5% DMSO). Test samples can also be measured over a concentration range of 0.1 to 4.0 mg/ml. For example neo-peptides are in that case dissolved in DMSO at 20 mg/ml and subsequently diluted 5, 10, 20 and 200 times to arrive at 4.0, 2.0, 1.0, and 0.1 mg/ml with TRIS-buffer.

The turbidimetry assay is thus based on Ph Eur 2.2.1 for determining the clarity of a sample. If the neo-peptide is insoluble, aggregates or particles are formed, these are measured by investigating the increased scattering when light moves through the sample at 620 nm. The measured value is then compared to a standard curve and a final NTU score is determined reporting on solubility of the single peptide. One procedure for determining single peptide solubility is as follows:

Single Peptides weighed and dissolved at 20 mg/ml in DMSO 1.0 mg/mL sample: 25 µl 20 mg/ml sample is diluted in 475 µl 25 mM TRIS pH=7.4 to 1.0 mg/ml (5% Final DMSO)

0.1 mg/mL sample: 2.5 µl 20 mg/ml sample is diluted in 497.5 µl 25 mM TRIS pH=7.4 to 0.1 mg/ml (0.5% Final DMSO)

100 ul diluted sample in ELISA plate reading optical density at 620 nm to report on aggregation Calculation of the NTU value using a linear regression of the standard curve A further solubility assay is performed on mixtures of a plurality of neo-peptides to provide for preferred neo-peptides in the liposomal composition: it is preferred that the at least one neo-peptide exhibits at most 50% reduction in its concentration when subjected to sterile filtration when present in a mixture of a plurality of neo-peptides and 25 mM TRIS pH 7.4 containing 5% (v/v) DMSO, wherein each of the plurality of peptides have a concentration of 0.1 mg/ml in the mixture prior to sterile filtration. This approach provides for exclusion from the liposomal composition of neo-peptides that would prove less suitable in a vaccine because they would aggregate with other neo-peptides, something the above turbidimetry test on single neo-peptides cannot be readily used to establish.

In general, the present method relies on use of a plurality of neo-peptides in order for the vaccine to be as effective as possible. Typically, the number of neo-peptides in the liposomal composition is selected from 2, 3, 4, 5, 6, 7, 8, 9, 10, 11, 12, 13, 14, 15, 16, 17, 18, 19, 20, 21, 22, 23, 24, 25, 26, 27, 28, 29, and 30 neo-peptides, but the number may in principle be as high as the physicochemical properties of the liposomal composition allows.

The plurality of neo-peptides is identified in one of several ways known to the skilled person. The simplest approach is to sequence (typically via "deep sequencing") the genome(s) from samples of the patient's malignant cells, and comparing in silico with a whole genome sequencing (also typically via "deep sequencing") result from the patient's normal cell(s) or from a standard "healthy" genome. Subsequently, the differences in the two sequence data set are analysed for mutation candidates that 1) are expressed (i.e. part of open reading frames) and 2) provide for expression products that include T-cell epitopes not normally found in the patient (neo-epitopes). For this end, data concerning the MHC typing of the patient is typically included to ensure that prediction of T-cell epitopes only provides correctly MHC-restricted sequences. An overview of T-cell epitope prediction methods, including MHC-binding predictions can e.g. be found in Desay D V and Kulkami-Kale U (2014), Methods Mol Biol 1184: 333-364 (doi: 10.1007/978-1-4939-1115-8_19) and Soria-Guerra R E et al. (2015), Journal of Biomedical Informatics 53: 405-414 (doi: 10.1016/j.jbi.2014.11.003).

In order to optimize the identification and selection of the neo-epitopes, any of the prediction methods available for this purpose are in practice useful. One example of a state of the art prediction algorithm is NetMHCpan-4.0 cbs.dtu.dk/ services/NetMHCpan-4.0/; Jurtz V et al., J Immunol (2017), ji1700893; DOI: 10.4049/jimmunol.1700893). This method is trained on a combination of classical MS derived ligands and pMHC affinity data. Another example is NetMHCstabpan-1.0 cbs.dtu.dk/services/NetMHCstabpan-1.0/; Rasmussen M et al., Accepted for J of Immunol, June 2016). This method is trained on a dataset of in vitro pMHC stability measurement using an assay where each peptide is synthesized and complexed to the MHC molecule in vitro. No cell processing is involved in this assay and the environment where the pMHC stability is measured is somewhat artificial. The method is in general less accurate than NetMHCpan-4.0. U.S. Pat. No. 10,055,540 describes a method for identification of neo-epitopes using classical MS detected ligands. Other patent application publications using similar technology are WO 2019/104203, WO 2019/075112, WO 2018/195357 (MHC Class II specific), and WO 2017 106638. Finally, MHCflurry: (DOI: doi.org/10.1016/j.cels.2018.05.014; github.com/openvax/mhcflurry) is like NetMHCpan trained on MS detected ligand data and pMHC affinities. A peptide-MHC Class II interaction prediction method is also disclosed in a recent publication Garde C et al., Immunogenetics, DOI: doi.org/10.1007/s00251-019-01122-z. In this publication, naturally processed peptides eluted from MHC Class II are used as part of the training set and assigned the binding target value of 1 if verified as ligands and 0 if negative.

Generally, these prediction systems employ artificial neural networks (ANNs): ANNs can identify non-linear correlations: Quantification of non-linear correlations is not an easy task, since it is difficult to calculate by simple calculation. This is primarily due to non-linear correlations described with more parameters than linear correlations and probably first appear when all features are considered collectively. Hence it is needed to take all features into account in order to catch the dependency across features.

In order to further improve the likelihood that the selected neo-epitopes provide for an effective immune response, use can preferably be made of the technology disclosed in European patent application nos. 19197295.9 and 19197306.4, both filed on 13 Sep. 2019. These applications disclose technologies, which enables that stability of binding between peptides and MHC molecules can be determined and which enables that stability of MHC binding of neo-epitopes is determined as part of the neo-epitope detection and selection. In brief, the data obtained from stability determinations are e.g. used as part of the training set for an ANN, and the ANN can subsequently rank identified peptides according to their predicted binding stabilities towards relevant MHC molecules.

Hence, it is according to the invention preferred that the at least one neo-peptide discussed herein includes a neo-epitope, which exhibits an MHC binding stability, which is above average, such as in the top quartile, among neo-epitopes identified in the neoplastic cells.

This particular choice of the neo-epitopes to include in the neopeptides is facilitated by the technologies disclosed in European patent application nos. 19197295.9 and 19197306.4. According to the present invention, identified (long) neo-peptides can when convenient be prepared as truncated versions in order to optimize characterization and/or production and/or stability of the end-product ultimately administered to the patient. The following truncation rules are therefore in general applied for any identified neopeptide in this preferred embodiment:

If the neopeptide contains a C anywhere in the sequence, it is truncated to remove the C and preferably maintain the longest fragment of the original neoepitope. For example as follows:

```
QIETQCRKFKASRASILSEMKMLKEKR (SEQ ID NO: 17)
            →
RKFKASRASILSEMKMLKEKR (SEQ ID NO: 18)
```

If there is a Q or N at the N-terminus, the Q/N is removed, for example as follows:

```
QIETQQRKFKASRASILSEMKMLKEKR (SEQ ID NO: 19)
            →
IETQQRKFKASRASILSEMKMLKEKR (SEQ ID NO: 20)
and
```

-continued

```
NIETQQRKFKASRASILSEMKMLKEKR (SEQ ID NO: 21)
            →
IETQQRKFKASRASILSEMKMLKEKR (SEQ ID NO: 20)
```

If the neopeptide contains a DG motif at the N-terminus, the D is removed, leaving the G, for example as follows.

```
DGETQQRKFKASRASILSEMKMLKEKR (SEQ ID NO: 22)
            →
GETQQRKFKASRASILSEMKMLKEKR (SEQ ID NO: 23)
```

Consequently the neopeptides discussed herein as useful immunogens in the composition disclosed herein will be free from cysteine residues and/or it will be free from Q and N as the N-terminal amino acid residue and/or it will be free from the amino acid sequence DG in the N-terminus. In a particular preferred embodiment, no neopeptide in the composition will include will comprise cysteine residue(s) and no neopeptide in the composition will include Q or N as the N-terminal amino acid residue and no neopeptide in the composition will include the amino acid sequence DG in its N-terminus Subsequent to the identification, the (plurality of) neopeptides are synthesized and preferably subjected to the above-discussed methods for determination of solubility prior to being incorporated in the liposomal formulation.

In some embodiments, the at least one neo-peptide is preferentially associated with the discontinuous phase in the liposomal composition, i.e. the at least one neo-peptide is entrapped in or coupled to the liposomes to a significantly higher degree than their presence in the continuous phase (the solvent). In other embodiments, the at least one neo-peptide is preferentially dissolved in the continuous phase of the liposomal composition instead of being associated with or bound to the liposomes in the liposomal composition.

Typically, the immunogenically effective amount is administered a plurality of times to the patient; typically this entails that the immunogenically effective amount is administered in a series of separate administrations separated by at least one day. In preferred embodiments of this aspect, the immunization scheme includes that the mammal (e.g. the human) receives one priming administration and one or more later booster administrations, but an equally attractive alternative is to use "cluster immunizations" i.e. an immunization scheme where repeated dosages of the immunogen(s) are administered at short intervals in the beginning of the immunization regimen before a memory immune response has been established; this is then followed by delay immunizations that resemble the traditional booster immunization used in a prime-boost immunization regimen.

In those cases where the immunogenically effective amount constitutes a relatively large volume of the composition discussed herein, it is advantageous to administer the immunogenically effective amount as several "sub-administration", i.e. by dividing the immunogenically effective amount into 2 more portions that each typically is administered at its own separate location in the patient. For instance, if a volume 2000 μl if the immunogenic composition is administered by means of injection, this will conveniently be done as 2 substantially simultaneous (i.e. within the same 12 hours) injections at different injections sites.

The liposomal composition can contain a pharmaceutically acceptable carrier. The term "pharmaceutically acceptable carrier" refers to a carrier for administration of a therapeutic agent, such as a polypeptide. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can also be used as excipients, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N. J. 1991).

Pharmaceutically acceptable carriers in the liposomal composition may contain liquids such as water, saline, glycerol and ethanol. Additionally, auxiliary substances, such as wetting or emulsifying agents, pH buffering substances, and the like, may be present in such vehicles. Typically, the liposomal compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

According to the first aspect of the invention, the solvent in the liposomal composition is typically aqueous, and preferably a buffered solvent holding a pH in the human physiological range. Since the neo-peptides are conveniently stored and initially dissolved in DMSO (dimethyl sulfoxide), this solvent component is present in the solvent of the liposomal composition, albeit preferably in relatively small concentrations. Further, the buffer used in the aqueous solvent is typically a TRIS (tris(hydroxymethyl)aminomethane) buffered aqueous solvent. Finally, the solvent can conveniently contain minor amounts of glycerol. Preferred liposomal compositions thus comprise less than 15% DMSO such as 10% DMSO, preferably <5% DMSO (v/v) and about 2% (v/v) glycerol. Further, the liposomal composition conveniently comprises TRIS in a concentration between 15 and 18 mM, preferably between 16.1 and 16.4 mM, but it should be underscored that the TRIS concentration is non-essential and can vary between e.g. 5 and 50 mM.

Typically, the liposomal composition has a pH in the range between 7.0 and 7.6, preferably about 7.4.

A particularly preferred liposomal composition used in the method of the first aspect of the invention comprises or consists of 1) a plurality of neo-peptides at a concentration of about 100 μg/ml per neo-peptide, 2) DMSO at a concentration of <5% (v/v), 3) about 1250 μg/ml DDA, 4) about 250 μg/ml MMG, 5) about 62.5 μg/ml poly(I:C), 6) about 2% (v/v) glycerol, and 7) TRIS at about pH 7.4 at about 16.25 mM.

When carrying out the method of the first aspect, the immunogenically effective amount of each of the neo-peptide(s) administered is preferably at least 10 μg, such as at least or at most 15, at least or at most 20, at least or at most 25, at least or at most 30, at least or at most 35, at least or at most 40, at least or at most 45, at least or at most 50, at least or at most at least or at most 55, at least or at most 60, at least or at most 65, at least or at most 70, at least or at most 75, at least or at most 80, at least or at most 85, at least or at most 90, at least or at most 95, at least or at most 100, at least or at most 105, at least or at most 110, at least or at most 115, at least or at most 120, at least or at most 125, at least or at most 130, at least or at most 135, at least or at most 140, at least or at most 145, at least or at most 150, at least or at most 155, at least or at most 160, at least or at most 165, at least or at most 170, at least or at most 175, at least or at most 180, at least or at most 185, at least or at most 190, at least or at most 195, at least or at most 200, at least or at most 205, at least or at most 210, at least or at most 215, at least or at most 220, at least or at most 225, at least or at most 230, at least or at most 235, at least or at most 240, at least or at most 245, at least or at most 250, at least or at most 255, at least or at most 260, at least or at most 265, at least or at most 270, at least or at most 275, at least or at most 280, at least or at most 285, at least or at most 290, at least or at most 295, at least or at most 300, at least or at most 305, at least or at most 310, at least or at most 315, at least or at most 320, at least or at most 325, at least or at most 330, at least or at most 335, at least or at most 340, at least or at most 345, at least or at most 350, at least or at most 355, at least or at most 360, at least or at most 365, at least or at most 370, at least or at most 375, at least or at most 380, at least or at most 385, at least or at most 390, at least or at most 395, and at least or at most 400 μg. Thus, preferably, the immunogenically effective amount of each of the peptide(s) administered is selected from the group consisting of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, and 400 μg.

Related to this, the volume of the liposomal composition administered per immunization to humans is typically between 400 and 2000 μl, with typical volumes being about 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990, and 2000 µl. As indicated above, each administration of the immunogenically effective amount of the liposomal composition can be made as at least 2 sub-administrations, in particular 2 sub-administrations per immunization; in this case the immunogenically effective amount is divided into the relevant number of fraction and each fraction is then typically administered at a separate location. For example, when 2000 µl is administered, this is preferably done as 2 sub-administrations of 1000 ml of the composition, preferably at separate locations in the patient.

As mentioned herein, the preferred vaccines of the invention induce cellular immunity, in particular induction of CD8$^+$ T-cell responses, in particular CTL responses, but also induction CD4$^+$ T-cell responses are of value.

With respect to the administration route, any convenient and effective route for administration of peptide based vaccines can be used. Preferred routes are the intradermal, the subcutaneous, the intraperitoneal, and the intramuscular routes, but also the intrapulmonary, intraocular, intrathecal, and intracerebral routes are possible.

Unit Dose of Composition—Second Aspect

The second aspect of the invention concerns a unit dose of a (liposomal) composition, said unit dose comprising an immunogenically effective amount of at least one peptide (neo-peptide), which comprises an amino acid sequence of a neo-epitope of a patient's neoplastic cells, a cationic liposomal adjuvant, and a buffered solvent. In general, the properties and constituents of the composition of the unit dose correspond to those of the composition used in the first aspect of the invention, and in general all considerations and details pertaining to the above-disclosed liposomal composition apply mutatis mutandis to the composition forming the unit dose.

Hence, in line with the fact that the method entails administration of certain preferred amounts of the neo-peptides discussed above, the unit dose preferably comprises at least 10 µg, such as at least or at most 15, at least or at most 20, at least or at most 25, at least or at most 30, at least or at most 35, at least or at most 40, at least or at most 45, at least or at most 50, at least or at most at least or at most 55, at least or at most 60, at least or at most 65, at least or at most 70, at least or at most 75, at least or at most 80, at least or at most 85, at least or at most 90, at least or at most 95, at least or at most 100, at least or at most 105, at least or at most 110, at least or at most 115, at least or at most 120, at least or at most 125, at least or at most 130, at least or at most 135, at least or at most 140, at least or at most 145, at least or at most 150, at least or at most 155, at least or at most 160, at least or at most 165, at least or at most 170, at least or at most 175, at least or at most 180, at least or at most 185, at least or at most 190, at least or at most 195, at least or at most 200, at least or at most 205, at least or at most 210, at least or at most 215, at least or at most 220, at least or at most 225, at least or at most 230, at least or at most 235, at least or at most 240, at least or at most 245, at least or at most 250, at least or at most 255, at least or at most 260, at least or at most 265, at least or at most 270, at least or at most 275, at least or at most 280, at least or at most 285, at least or at most 290, at least or at most 295, at least or at most 300, at least or at most 305, at least or at most 310, at least or at most 315, at least or at most 320, at least or at most 325, at least or at most 330, at least or at most 335, at least or at most 340, at least or at most 345, at least or at most 350, at least or at most 355, at least or at most 360, at least or at most 365, at least or at most 370, at least or at most 375, at least or at most 380, at least or at most 385, at least or at most 390, at least or at most 395, and at least or at most 400 µg of each neo-peptide, and preferably an amount selected from 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, and 400 µg of each neo-peptide—again with the proviso that the upper limit on the total mass of included neo-peptides is set by the physicochemical properties of the composition.

Also, in line with the preferred volumes of the liposomal composition administered, the unit dose preferably consists of between 400 and 2000 µl, such as 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990, and 2000 µl.

Also, the unit dose include a number of neo-peptides, which is preferably selected from 2, 3, 4, 5, 6, 7, 8, 9, 10, 11, 12, 13, 14, 15, 16, 17, 18, 19, 20, 21, 22, 23, 24, 25, 26, 27, 28, 29, and 30, even though the number may be higher if the physicochemical properties of the liposomal composition so permit.

Composition of the Invention—Third Aspect

It is believed that the liposomal composition that is used in the first aspect of the invention in its own right is inventive. Hence, the third aspect of the invention relates to a liposomal composition, which has been disclosed in the context of the first aspect of the invention and all disclosures made under the first aspect in so far as they relate to the properties and constituents of the liposomal composition appy mutatis mutandis to the third aspect of the invention.

Other Aspects

As will be apparent from the claims the present invention also relates to a unit dose of the second aspect or a composition of the third aspect for use in therapy, in particular for use in a method of the first aspect. Likewise, also embraced by the present invention is the use of a unit dose of the second aspect or a liposomal composition of the $3^{rd}$ aspect for the preparation of a pharmaceutical composition for use in any method of the first aspect of the invention.

Example 1

Induction of Neo-Epitope Specific T-Cell by Peptides in CAF09b Adjuvant

In two recent unpublished preclinical tumour studies (data not presented here), immunization with a vaccine consisting of the adjuvant CAF09b in admixture with 2.0 μg of each of a number of predicted neo-peptides was found not to inhibit the growth of tumours from which the neopeptides were derived.

In the present study, higher doses were tested of one neo-peptide (termed C22 herein). The minimal epitope in C22 has been defined, thus allowing for detection of neo-peptide specific CD8+ T-cells by MHC I multimer staining. C22 has the amino acid sequence QIETQQRKFKAS-RASILSEMKMLKEKR (SEQ ID NO: 1), where the minimal MHC Class I restricted epitope is constituted by the underlined 9 amino acids KFKASRASI (SEQ ID NO: 2).

The objectives of the present study thus were to:

i) Test whether high neo-peptide doses admixed with CAF09b induce neo-peptide specific splenic T cells ii) Test if neo-peptide specific CD8+ cells can be detected in non-enriched whole blood samples as this enables follow-up of the responses over time iii) Test whether "cluster priming" is superior to standard prime-boost immunization With a view to favour a CD8+ T cell immune response of peptide-based vaccines, Statens Serum Institute (SSI) has developed a cationic liposomal adjuvant, CAF09b that has been shown to induce both CD4+ and CD8+ T cells. The liposomes consist of the positively charged dimethyldiocta-decylammonium (DDA) to facilitate repulsion/stability and cell entry, monomycoloyl glycerol (MMG) as PAMP signal for CD4+ cell generation, and the Toll-like receptor 3 agonist polyinosinic:polycytidylic acid ("poly(I:C)") with the potential of inducing reactive cytotoxic T cells.

Neo-peptides were identified by whole exome sequencing of the mouse colon cancer cell line CT26 and normal tissue samples from BALB/c mice and by selecting peptides found only in the cancer cells.

The aim of the present experiment was to test if CAF09b-adjuvanted predicted neo-peptides could induce reactive T cells in mice.

In a publication by Wick D A et al. (2011), Vaccine 29(5):984-993, it has been reported that cluster priming with 3.7 μg of a 19 amino acid residue peptide derived from HPV16 E7 in admixture with Poly(I:C) was superior to conventional prime-boost immunisation. Additionally, in a recent paper by Ott P A et al. (2017), Nature 547(7662): 217-221, clinical responses were reported in melanoma patients cluster primed with neo-peptides in the Hiltonol adjuvant.

It was therefore hypothesised that cluster priming with neo-peptides would elicit a stronger response compared to standard prime-boost immunisation.

Materials and Methods

BALB/c Mice 6-8 weeks old BALB/c JrJ femal mice were acquired from Janvier Labs. The mice were acclimated for one week before initiation of the experiment. The mice had ad libitum access to water and standard chow pellets. The experiment was conducted under license 2017-15-0201-01338 from the Danish Animal Experimentation Inspectorate in accordance with the Danish Animal Experimentation Act, which is stricter and therefore fully compliant with the European directive (2010/63/EU). The mice were ear tagged to allow for identification of individuals.

Experimental Design—Allocation and Treatment of Mice

To avoid "cage effects" all treatment groups were represented in each cage. Mice in groups 1, 2, 3 and 4 (the cluster immunization groups) were intraperitoneally (i.p.) immunized at day 0, 1, 2, 3, 7, 14 and 21 with 0.4, 2.0, 10.0 and 50.0 μg of C22 admixed with CAF09b, respectively. Corresponding groups (5, 6, 7 and 8) were vaccinated according to a traditional prime-boost strategy on days 0, 14 and 21 with solutions identical to what group 1, 2, 3 and 4 received. Dosing volumes for the mice were 200 μl for all vaccines. See FIG. 1 for details.

Vaccine Formulation

The C22 peptide was synthesised by GenScript and aliquoted into 0.8 mg portions as a lyophilized product. The peptide was solubilized in DMSO to a concentration of 10 mg/ml by adding 80 μl DMSO to each aliquot. The peptide stock was then diluted 10 times in sterile water (80 μl peptide stock+720 μl sterile water). For each dosing day, peptides were prepared and stored at −20° C. until use. On the day of immunization, the peptides were thawed and TRIS buffer and CAF09b were added in the indicated volumes. The final vaccine for the mice contained 200 μg DDA, 40 μg MMG, and 10 μg Poly(I:C) per dose. For further details of the vaccine formulation, see the following table:

| | C22 dose | Volume C22 | Sterile water | TRIS | CAF09b |
|---|---|---|---|---|---|
| Group 1 | 0.4 | 2 | 88 | 500 | 400 |
| Group 2 | 2 | 10 | 90 | 500 | 400 |
| Group 3 | 10 | 50 | 50 | 500 | 400 |

-continued

| | C22 dose | Volume C22 | Sterile water | TRIS | CAF09b |
|---|---|---|---|---|---|
| Group 4 | 50 | 250 | — | 500 | 400 |
| Group 5 | 0.4 | 2 | 88 | 500 | 400 |
| Group 6 | 2 | 10 | 90 | 500 | 400 |
| Group 7 | 10 | 50 | 50 | 500 | 400 |
| Group 8 | 50 | 250 | — | 350 | 400 |

Generation of Single Cell Suspension from Spleens

At endpoint spleens from all mice in the study were collected. Single cell suspensions were generated according to the following protocol:

Materials

RPMI (Gibco RPMI 1640)

FCS (Gibco)

RBC lysis buffer 10× (BioLegend, #420301)

70 µm cell strainers (Corning, #43175)

GentleMACS C tubes (Miltenyi, #130-093-237)

50 ml tubes

Cryo vials

Apparatus

GentleMACS dissociator (Miltenyi)

LAF bench

Mr. Frosty or another freeze box

Procedure

1. Collect tissue into pre-labelled C tubes containing R10 (RPMI containing 10% FCS) Recommended: 3 ml of media per spleen. Store on ice until processing. Keep sterile.
2. Tightly close C tubes and attach upside down onto the sleeve of the gentleMACS dissociator. Run program m_spleen_01 (for 1-2 spleens per tube).
3. Optional: perform a short centrifugation of C tubes after dissociation to collect sample material at the bottom of the tubes.
4. Place a 70 µm cell strainer on top of a pre-labelled 50 ml tube and pre-wet with R10.
5. Resuspend sample containing C tubes and apply cell suspension to 70 µm cell strainers.
6. Optional: wash C tubes with 2 ml R10 and apply to cell strainers to get residual cells.
7. Flush cell strainer with 5 ml R10. Remember to pipette residual fluid from the bottom of the filter.
8. Centrifuge cells: 1500 rpm, 5 min @4° C. Pour off supernatant. Break the pellet.
9. Optional: Perform erythrocyte lysis using 1 ml of 1×RBCL buffer (stock 10×, diluted in PBS) for 2 min. Wash with 5 ml R10 to get cells out of RBCL buffer.
10. Resuspend in 1 ml R10 and count the cells.
11. Wash again with 5 ml R10.
   Optional: filter through an additional 70 µm cell strainer to get rid of debris if any.
12. Resuspend cells at an appropriate concentration (e.g. $20 \times 10^6$ cells/ml) in FCS+10% DMSO
13. Aliquot 1 ml cell suspension to pre-labeled cryo vials.
14. Transfer cells to Mr. Frosty and place at −80° C. for 24 hours before transferring to nitrogen storage.

To detect C22 specific CD8+ T cells, whole EDTA blood samples and splenocytes were stained with fluorescently labelled MHC I multimers loaded with the C22 derived minimal peptide KFKASRASI (SEQ ID NO: 2), identified as the strongest MHC I binder embedded in the 27 amino acid C22 sequence. The MHC I multimer assay is depicted in FIG. 2. The detailed staining protocol was as follows:

Materials

Eppendorf Tubes

Deep 96 well plate (2 ml, Sigma, #575653)

Lysing solution 10× (BD #349202)

MHC multimers, C22 APC and PE labelled and irrelevant (C30) APC and PE labelled

FACS buffer (PBS+2% FCS)

Procedure

1. Draw blood from mice: Vein puncture (tail or v. saphena) into EDTA coated tubes—BD Vacutainer EDTA blood collection tubes
2. Stain 50 µl of blood in a deep 96 well plate, according to plate setup
3. Spin of multimers after thawing (quick spin)
4. Dilute 1 µl of each multimer in 29 µl FACS buffer (per samples) in an eppendorf tube
5. Spin multimer eppendorf tube (3300 g, 5 min).
6. Add 30 µl diluted multimer, according to plate setup. Add 30 ul FACS buffer to "no multimer samples" ac-cording to the plate setup
   6.1. Avoid the pellet in the multimer tube as this possibly contains aggregates of MHC multimers
7. Add 50 µl FACS buffer to setup samples according to plate setup
8. Incubate for 15 min@37° C. in the dark
9. Block FC binding by adding 1 µl anti-CD16/CD32, incubate for 10 min@RT in the dark
10. Make antibody master mix according to calculations—see appendix 2
11. Add 20 µl antibody master mix to the wells for staining according to plate setup
12. Incubate 30 minutes at 4° C.
13. Add 1 ml lysing/fixation solution (diluted in H2O) per well to lyse red blood cells. Incubate for 5-10 minutes@RT in the dark
14. Wash 2 times in FACS buffer (spin 1500 rpm 5 min)
15. Transfer to FACS tubes in 200 µl FACS buffer
16. Analyze on flow cytometer.

Results

Detection of Circulating Neo-Peptide Specific CD8+ T Cells

At day 21 EDTA blood was collected and stained with MHC I multimers according to the assay outlined above and in FIG. 2. Only samples from two mice in each group were analysed as this was the first attempt to detect neo-peptide specific CD8+ T cells in whole blood samples; the analysis was thus considered a pilot experiment. At endpoint (day 28) blood from all mice in the experiment was sampled.

At day 21, a dose-dependent response was observed with both cluster priming and the standard prime-boost schedule; neo-peptide specific CD8+ T cells were detected in mice dosed with 10.0 and 50.0 µg C22 admixed with CAF09b, whereas lower doses did not elicit any neo-peptide specific CD8+ T cells (see FIG. 3). At endpoint, the responses were similar to day 21 even though the mice had been boosted one additional time (see FIG. 4). Noteworthy, at endpoint low-frequency MHC:C22 positive CD8+ T cells were detected in blood from mice cluster primed with 2.0 µg C22 as opposed to the standard prime-boost schedule where hardly any neo-peptide specific CD8+ cells were seen.

To test the specificity of assay, blood from mice receiving CAF09b were stained with the MHC:C22 multimers. In these samples, no signal was detected. Likewise, blood samples stained with MHC I tetramers loaded with an irrelevant peptide (termed "C25") derived from the neo-peptides were negative, indicating that the assay was highly specific.

Detection of Neo-Peptide Specific Splenic CD8+ T Cells

At termination 28 days post first immunization, spleens from the mice were collected and single cells suspension were prepared and stored at −80° C. Additionally, spleens from two naïve mice and two mice i.p. dosed with CAF09b were included.

Only splenocytes from cluster primed mice were analysed at the day of termination. Neo-peptide specific CD8+ T cells were detected in spleens from mice immunised with 10.0 and 50.0 µg C22+CAF09b, whereas lower doses did not induce a detectable response. Similar to what was observed in whole blood samples, neo-peptide specific CD8+ T cells were not detected in CAF09b dosed mice. Additionally, no signal was observed when staining the splenocytes with MHC tetramers loaded with an irrelevant peptide (termed "C25"). See FIG. 5.

Animal Well-being

To monitor the impact of the vaccine on the general well-being of the mice, the animals were closely inspected after receiving the vaccines and weighed at least three times a week during the entire experiment. Immediately after the immunizations, the mice showed signs of abdominal pain that resolved within 1-2 hours, where after they returned to normal behaviour. Sequential daily immunizations did not impact the well-being of the mice significantly compared to standard prime-boost. In both sets of experiments, the mice lost approximately 5% of their initial body weight after immunization 1, but subsequent immunizations did not affect the body weight (data not shown).

Discussion

Immunization with 10.0 and 50.0 µg C22 admixed with CAF09b robustly induced neo-peptide specific CD8+ cells identified by MHC I tetramer staining, whereas lower doses surprisingly did not. On the other hand, no significant advantage of cluster priming compared to a conventional prime-boost schedule was observed. However, a small increase in the response to 2.0 µg C22 was observed with cluster priming compared to conventional prime-boost.

Mice immunized with CAF09b-containing vaccines lost approximately 5% of their initial body weight, indicative of physiologically active components in the vaccine. The impact of the vaccine on the general well-being of the mice was considered acceptable as the body weight loss was transient and all mice returned to baseline within 3-4 days for both the cluster priming and prime-boost methodology.

Example 2

Preliminary Clinical Trial Data

A phase 1/2a clinical trial to test the present inventions approach in targeting neo-epitopes was initiated with the first dosing of a patient in Marts 2019. The trial includes patients suffering from malignant melanoma, non-small cell lung cancer (NSCLC) and bladder cancer.

In brief, the treatment entails that a panel of neo-epitopes derived from malignant cells are identified in each of the enrolled patients, where after the neo-epitopes are synthesized, formulated and administered to the patients according to the present invention; first, 3 immunizations are made at 2 weeks interval intraperitoneally, and subsequently 3 intramuscular immunizations are made at 2 weeks interval following a 2 weeks pause from the final intraperitoneally dose. Hence, all vaccinations are given in 2 preferable weeks intervals.

The following data is obtained from 2 patients after conclusion of the intraperitoneal immunizations but prior to the intramuscular immunizations.

| | Baseline Blood sample | 1. IP Immu-nization | 2. IP Immu-nization | 3. IP Immu-nization | Post IP vaccination blood sample |
|---|---|---|---|---|---|
| Patient 1 | Day 0 | Day 0 | Day 14 | Day 25 | Day 42 |
| Patient 2 | Day 0 | Day 0 | Day 20 | Day 34 | Day 48 |

Patients 1 and 2 each received their 3 intraperitoneal immunizations with a vaccine prepared from a pool of peptides that had been identified as neo-epitope containing amino acid sequences in malignant tissue in the patient:

For patient 1, the peptide pool was comprised of the following 9 peptides (SEQ ID NOs: 3-11) solubilized in DMSO:

| Peptide label | Peptide Sequence | Theor. MW (u) | Batch No. |
|---|---|---|---|
| CA018 | H-PLRDGGAKIDGYIISYREEEQPADRWT-OH | 3136.5 | SMX-0260 |
| CA019* | H-ILVLESSVQGYPTQRARYQWVR-OH | 2650.1 | SMX-0261 |
| CA022 | H-SKQQDSDKLNSLSIPSVSKRVVLGDSV-OH | 2887.3 | SMX-0262 |
| CA024 | H-TGPESRREVPVYTYSEPRQEVPM-OH | 2708.0 | SMX-0264 |
| CA030 | H-KVGNNSSHFLQPNLRGPLFL-OH | 2238.6 | SMX-0267 |
| CA031 | H-WSSSRRSRSSYTHSLNRTGFYRHSG-OH | 2973.2 | SMX-0268 |
| CA032 | H-HQPEAIEEFPVPAFHHPVFQQESFTRQ-OH | 3233.6 | SMX-0269 |

-continued

| Peptide label | Peptide Sequence | Theor. MW (u) | Batch No. |
|---|---|---|---|
| CA035 | H-FVTELELFEVQPLASGDYS-OH | 2144.4 | SMX-0272 |
| CA036 | H-DREKIYQWINELSGPETRENALLELSK-OH | 3232.6 | SMX-0273 |

For patient 2, the peptide pool was comprised of the following 5 peptides (SEQ ID NOs: 12-16) solubilised in DMSO:

| Peptide label | Peptide Sequence | Theor. MW (u) | Batch No. |
|---|---|---|---|
| CA063 | H-DKIGPVDHIEFFSGPEFKKTLASKT-OH | 2792.2 | SMX-0288 |
| CA064* | H-VKTRMQSLQPDLAARYRNVLEALWR-OH | 3015.6 | SMX-0289 |
| CA070* | H-HRFEREDVDDIKVYSPYEISIRQRFIG-OH | 3368.8 | SMX-0294 |
| CA071* | H-LLASGRAPRRASSALPRNTVVLFVPQQ-OH | 2905.4 | SMX-0295 |
| CA073* | H-YVKAEKNVPDLKSIYNNVLQLIKVNFS-OH | 3137.7 | SMX-0297 |

Peptides marked with asterisks were included in the respective pools at about the double concentration compared to the remaining peptides. Measured concentrations of the low concentration peptides ranged between 1.6 and 1.8 mg/ml, whereas the high concentration peptides had concentrations ranging between 3.1 and 3.5 mg/ml.

Vaccines were prepared by diluting 0.12 ml of the patient's peptide pool composition with 1.08 ml 25 mM TRIS buffer. From this solution, 1 ml TRIS buffered pool dilution was add mixed with 1 ml CAF09b to produce the vaccine composition. For the IP injections at 1× dosage, 0.50 ml of the vaccine composition was injected intraperitoneally per immunization.

Just prior to the first intraperitoneal immunization, blood was collected from each patient and the same was the case after the 3 intraperitoneal immunizations just prior to the first intramuscular immunization. PBMC cells from these blood samples were thus subjected to pre-immunization and post peritoneal immunization ELISPOT assays and ICS/Restimulation assays.

The ELISPOT assay is a standard technique for indirect detection of reactive T-cells where a secreted cytokine (in this case IFNγ) is measured in an ELISA like setup upon stimulation of peripheral blood mononuclear cells (PBMCs) isolated from the patient with each of the peptides of the vaccine.

In the ICS/Restimulation assay, PBMCs from the patient are stimulated with the entire pools of vaccine peptides and subsequently subjected to flowcytometric cell counting, where they are tested for the presence of cell surface markers (CD3, CD4, CD8) and cytokines (IFNγ and TNFα) to detect the presence of T cell subpopulations that release the cytokines.

Results from these experiments can be summarized as follows:

Patient 1: In the pre-immunzation experiments, neither the IFNγ ELISPOT nor the ICS/re-stimulation assay demonstrated the presence of significant numbers of reactive T-cells against any of the vaccine peptides when compared to positive controls (data not shown). In contrast, the post intraperitoneal immunization experiment demonstrated the presence of reactive T-cells against 4 of 9 vaccine peptides in the ELISPOT assay (See FIG. 6A) and the presence of IFN-γ and TNF-α CD4+ cells (FIG. 6G) but not CD8+ cells (data not shown) in the ICS/restimulation assay. The strongest IFN-γ response in the ELISPOT was found for the double dosage peptide.

Patient 2: In the pre-immunization experiments, neither the IFNγ ELISPOT nor the ICS/re-stimulation assay demonstrated the presence of significant numbers of reactive T-cells against any of the vaccine peptides when compared to positive controls (See FIGS. 7A and 7C, the latter only showing data for CD4+ cells). In contrast, the post intraperitoneal immunization experiment demonstrated the presence of reactive T-cells against 3 of 5 vaccine peptides in the ELISPOT assay (see FIG. 7B) and the presence of IFN-γ and TNF-α CD4+ cells (FIG. 7D) but not CD8+ cells (data not shown) in the ICS/restimulation assay. The strongest IFN-γ response in the ELISPOT was found for the double dosage peptides.

It can be concluded that in both patients, the neo-epitope containing cocktail vaccine induces an adaptive immune response.

The invention claimed is:

1. A unit dose of an immunogenic composition, said unit dose comprising an immunogenic effective amount of at least one peptide (non-peptide), which comprises an amino acid sequence of a neo-epitope of a patient's neoplastic cells, a cationic liposomal adjuvant, and a solvent, wherein the cationic liposomal adjuvant comprises dimethyldioctadecylammonium (DDA), polyinosinic acid:polycytidylic acid (poly(I:C)), and MMG, wherein MMG is monomycolyl glycerol or its synthetic analogue 3-hydroxy-2-tetradecyl-octadecanoic acid-2,3-dihydroxypropyl ester, and wherein the unit dose comprises at least 100 μg of each of said at least one neo-peptide.

2. The unit dose according to claim 1, which comprises at least 100 μg, at least or at most 105 μg, at least or at most 110 μg, at least or at most 115 μg, at least or at most 120 μg, at least or at most 125 μg, at least or at most 130 μg, at least or at most 135 μg, at least or at most 140 μg, at least or at most 145 μg, at least or at most 150 μg, at least or at most 155 μg, at least or at most 160 μg, at least or at most 165 μg, at least or at most 170 μg, at least or at most 175 μg, at least or at most 180 μg, at least or at most 185 μg, at least or at most 190 μg, at least or at most 195 μg, at least or at most 200 μg, at least or at most 205 μg, at least or at most 210 μg, at least or at most 215 μg, at least or at most 220 μg, at least or at most 225 μg, at least or at most 230 μg, at least or at most 235 μg, at least or at most 240 μg, at least or at most 245 μg, at least or at most 250 μg, at least or at most 255 μg, at least or at most 260 μg, at least or at most 265 μg, at least or at most 270 μg, at least or at most 275 μg, at least or at most 280 μg, at least or at most 285 μg, at least or at most 290 μg, at least or at most 295 μg, at least or at most 300 μg, at least or at most 305 μg, at least or at most 310 μg, at least or at most 315 μg, at least or at most 320 μg, at least or at most 325 μg, at least or at most 330 μg, at least or at most 335 μg, at least or at most 340 μg, at least or at most 345 μg, at least or at most 350 μg, at least or at most 355 μg, at least or at most 360 μg, at least or at most 365 μg, at least or at most 370 μg, at least or at most 375 μg, at least or at most 380 μg, at least or at most 385 μg, at least or at most 390 μg, at least or at most 395 μg, or at least or at most 400 μg of each neo-peptide.

3. The unit dose according to claim 2, which comprises an amount selected from 100 μg, 101 μg, 102 μg, 103 μg, 104 μg, 105 μg, 106 μg, 107 μg, 108 μg, 109 μg, 110 μg, 111 μg, 112 μg, 113 μg, 114 μg, 115 μg, 116 μg, 117 μg, 118 μg, 119 μg, 120 μg, 121 μg, 122 μg, 123 μg, 124 μg, 125 μg, 126 μg, 127 μg, 128 μg, 129 μg, 130 μg, 131 μg, 132 μg, 133 μg, 134 μg, 135 μg, 136 μg, 137 μg, 138 μg, 139 μg, 140 μg, 141 μg, 142 μg, 143 μg, 144 μg, 145 μg, 146 μg, 147 μg, 148 μg, 149 μg, 150 μg, 151 μg, 152 μg, 153 μg, 154 μg, 155 μg, 156 μg, 157 μg, 158 μg, 159 μg, 160 μg, 161 μg, 162 μg, 163 μg, 164 μg, 165 μg, 166 μg, 167 μg, 168 μg, 169 μg, 170 μg, 171 μg, 172 μg, 173 μg, 174 μg, 175 μg, 176 μg, 177 μg, 178 μg, 179 μg, 180 μg, 181 μg, 182 μg, 183 μg, 184 μg, 185 μg, 186 μg, 187 μg, 188 μg, 189 μg, 190 μg, 191 μg, 192 μg, 193 μg, 194 μg, 195 μg, 196 μg, 197 μg, 198 μg, 199 μg, 200 μg, 201 μg, 202 μg, 203 μg, 204 μg, 205 μg, 206 μg, 207 μg, 208 μg, 209 μg, 210 μg, 211 μg, 212 μg, 213 μg, 214 μg, 215 μg, 216 μg, 217 μg, 218 μg, 219 μg, 220 μg, 221 μg, 222 μg, 223 μg, 224 μg, 225 μg, 226 μg, 227 μg, 228 μg, 229 μg, 230 μg, 231 μg, 232 μg, 233 μg, 234 μg, 235 μg, 236 μg, 237 μg, 238 μg, 239 μg, 240 μg, 241 μg, 242 μg, 243 μg, 244 μg, 245 μg, 246 μg, 247 μg, 248 μg, 249 μg, 250 μg, 251 μg, 252 μg, 253 μg, 254 μg, 255 μg, 256 μg, 257 μg, 258 μg, 259 μg, 260 μg, 261 μg, 262 μg, 263 μg, 264 μg, 265 μg, 266 μg, 267 μg, 268 μg, 269 μg, 270 μg, 271 μg, 272 μg, 273 μg, 274 μg, 275 μg, 276 μg, 277 μg, 278 μg, 279 μg, 280 μg, 281 μg, 282 μg, 283 μg, 284 μg, 285 μg, 286 μg, 287 μg, 288 μg, 289 μg, 290 μg, 291 μg, 292 μg, 293 μg, 294 μg, 295 μg, 296 μg, 297 μg, 298 μg, 299 μg, 300 μg, 301 μg, 302 μg, 303 μg, 304 μg, 305 μg, 306 μg, 307 μg, 308 μg, 309 μg, 310 μg, 311 μg, 312 μg, 313 μg, 314 μg, 315 μg, 316 μg, 317 μg, 318 μg, 319 μg, 320 μg, 321 μg, 322 μg, 323 μg, 324 μg, 325 μg, 326 μg, 327 μg, 328 μg, 329 μg, 330 μg, 331 μg, 332 μg, 333 μg, 334 μg, 335 μg, 336 μg, 337 μg, 338 μg, 339 μg, 340 μg, 341 μg, 342 μg, 343 μg, 344 μg, 345 μg, 346 μg, 347 μg, 348 μg, 349 μg, 350 μg, 351 μg, 352 μg, 353 μg, 354 μg, 355 μg, 356 μg, 357 μg, 358 μg, 359 μg, 360 μg, 361 μg, 362 μg, 363 μg, 364 μg, 365 μg, 366 μg, 367 μg, 368 μg, 369 μg, 370 μg, 371 μg, 372 μg, 373 μg, 374 μg, 375 μg, 376 μg, 377 μg, 378 μg, 379 μg, 380 μg, 381 μg, 382 μg, 383 μg, 384 μg, 385 μg, 386 μg, 387 μg, 388 μg, 389 μg, 390 μg, 391 μg, 392 μg, 393 μg, 394 μg, 395 μg, 396 μg, 397 μg, 398 μg, 399 μg, and 400 μg of each neo-peptide.

4. The unit dose according to claim 1, wherein the number of neo-peptides is selected from 2, 3, 4, 5, 6, 7, 8, 9, 10, 11, 12, 13, 14, 15, 16, 17, 18, 19, 20, 21, 22, 23, 24, 25, 26, 27, 28, 29, and 30.

5. The unit dose according to claim 1, wherein the ratio DDA:MMG is 5:1 by (w/w), and wherein the ratio DDA: poly(I:C) is between 5:1 and 20:1 (w/w).

6. The unit dose according to claim 1, wherein the DDA:MMG:poly(I:C) relative weights are 5:1:1.

7. The unit dose according to claim 1, wherein the DDA:MMG:poly(I:C) relative weights are 20:4:1.

8. The unit dose according to claim 1, wherein the at least one neo-peptide is free from cysteine residues.

9. The unit dose according to claim 1, wherein the at least one neo-peptide is free from Q and N as the N-terminal amino acid residue.

10. The unit dose according to claim 1, wherein the at least one neo-peptide is free from the amino acid sequence DG in the N-terminus.

11. The unit dose according to claim 1, wherein the immunogenic composition has a pH in the range between 7.0 and 7.6.

12. The unit dose according to claim 11, wherein the pH is about 7.4.

13. A method for treatment of a neoplasm, in a mammalian patient, wherein the neoplasm exhibits T-cell epitopes (neo-epitopes) that are not exhibited by non-neoplastic cells in the patient, the method comprising administering an immunogenically effective amount of a liposomal composition comprising
  1) at least one peptide (neo-peptide), which comprises an amino acid sequence of a neo-epitope of the patient's neoplastic cells,
  2) a solvent, and
  3) a cationic liposomal adjuvant
  wherein the cationic liposomal adjuvant comprises dimethyldioctadecylammonium (DDA), polyinosinic acid: polycytidylic acid (poly(I:C)), and MMG, wherein MMG is monomycolyl glycerol or its synthetic analogue 3-hydroxoy-2-tetradecyl-octadecanoic acid-2,3-dihydroxypropyl ester, and wherein the amount of each of the neo-peptide(s) administered is at least 100 µg.

14. The method according to claim 13, wherein the ratio DDA:MMG is 5:1 by (w/w), and wherein the ratio DDA:poly(I:C) is between 5:1 and 20:1 (w/w).

15. The method according to claim 13, wherein the DDA:MMG:poly(I:C) relative weights are 5:1:1.

16. The method according to claim 13, wherein the DDA:MMG:poly(I:C) relative weights are 20:4:1.

17. The method according co claim 13, wherein the at least one neo-peptide is water-soluble wherein
  1.0 mg/ml neo-peptide in 25 mM TRIS pH 7.4 containing 5% (v/v) DMSO provides for an NTU (nephelometric turbidity unit) of at most 50, and
  1.0 mg/ml neo-peptide in 25 mM TRIS pH 7.4 and 0.5% (v/v) DMSO provides for an NTU of at most 25.

18. The method according to claim 13, wherein the at least one neo-peptide exhibits at most 50% reduction in its concentration when in a mixture of a plurality subjected filtration to sterile when present in a mixture of a plurality of neo-peptides and 25 mM TRIS pH 7.4 containing 5% (v/v) DMSO, wherein each of the plurality of peptides have a concentration of 0.1 mg/ml in the mixture prior to sterile filtration.

19. The method according to claim 13, wherein the number of neo-peptides is selected from 2, 3, 4, 5, 6, 7, 8, 9, 10, 11, 12, 13, 14, 15, 16, 17, 18, 19, 20, 21, 22, 23, 24, 25, 26, 27, 28, 29, and 30 neo-peptides.

20. The method according to claim 13, wherein the at least one neo-peptide includes a neo-epitope, which exhibits all MHC binding stability, which is above average, among neo-epitopes identified in the neoplastic cells.

21. The method according to claim 13, wherein the at least one neo-peptide is free from cysteine residues.

22. The method according to claim 13, wherein the at least one neo-peptide is free from Q and N as the N-terminal amino acid residue.

23. The method according to claim 13, wherein the at least one neo-peptide is free from the amino acid sequence DG in the N-terminus.

24. The method according to claim 13, wherein the at least one neo-peptide is entrapped in or coupled to liposomes in the cationic liposomal adjuvant to a higher degree than it is dissolved in the solvent in the liposomal composition.

25. The method according to claim 16, wherein the at least one neo-peptide is the liposomal composition.

26. The method according to claim 13, wherein the immunogenically effective amount is administered a plurality of times to the patient.

27. The method according to claim 26, wherein separate administrations are separated by at least one day.

28. The method according to claim 13, wherein the liposomal composition has a pH in the range between 7.0 and 7.6.

29. The method according to claim 28, wherein the pH is about 7.4.

30. The method according to claim 16, wherein the immunologically effective amount of each of the neo-peptide(s) administered is at least 105 µg, at least or at most 110 µg, at least or at most 115 µg, at least or at most 120 µg, at least or at most 125 µg, at least or at most 130 µg, at least or at most 135 µg, at least or at most 140 µg, at least or at most 145 µg, at least or at most 150 µg, at least or at most 155 µg, at least or at most 160 µg, at least or at most 165 µg, at least or at most 170 µg, at least or at most 175 µg, at least or at most 180 µg, at least or at most 185 µg, at least or at most 190 µg, at least or at most 195 µg, at least or at most 200 µg, at least or at most 205 µg, at least or at most 210 µg, at least or at most 215 µg, at least or at most 220 µg, at least or at most 225 µg, at least or at most 230 µg, at least or at most 235 µg, at least or at most 240 µg, at least or at most 245 µg, at least or at most 250 µg, at least or at most 255 µg, at least or at most 260 µg, at least or at most 265 µg, at least or at most 270 µg, at least or at most 275 µg, at least or at most 280 µg, at least or at most 285 µg, at least or at most 290 µg, at least or at most 295 µg, at least or at most 300 µg, at least or at most 305 µg, at least or at most 310 µg, at least or at most 315 µg, at least or at most 320 µg, at least or at most 325 µg, at least or at most 330 µg, at least or at most 335 µg, at least or at most 340 µg, at least or at most 345 µg, at least or at most 350 µg, at least or at most 355 µg, at least or at most 360 µg, at least or at most 365 µg, at least or at most 370 µg, at least or at most 375 µg, at least or at most 380 µg, at least or at most 385 µg, at least or at most 390 µg, at least or at most 395 µg, or at least or at most 400 µg.

31. The method according to claim 16, wherein immunogenically effective amount of each of the peptide(s) administered is selected from the group consisting of 100, 101, 102, 103, 104, 105, 106, 107, 108, 109, 110, 111, 112, 113, 114, 115, 116, 117, 18, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152,153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, and 400 µg.

32. The method according to claim 16, wherein each administration of the immunogenically effective amount of the liposomal composition is made as at least 2 sub-administrations.

33. The method according to claim 32, wherein 2000 µl is administered as 2 sub-administrations of 1000 µl.

34. The method according to claim 32, wherein the at least 2 sub-administrations are 2 sub-administrations per immunization.

35. The method according to claim 13, wherein the neoplasm is a malignant neoplasm.

\* \* \* \* \*